United States Patent
Georges et al.

(10) Patent No.: US 12,383,723 B2
(45) Date of Patent: Aug. 12, 2025

(54) MAMMALIAN BODY IMPLANTABLE FLUID FLOW INFLUENCING DEVICE

(71) Applicant: Puzzle Medical Devices Inc., Montreal (CA)

(72) Inventors: Gabriel Georges, Quebec (CA); François Trudeau, Quebec (CA)

(73) Assignee: Puzzle Medical Devices Inc., Montreal (CA)

( * ) Notice: Subject to any disclaimer, the term of this patent is extended or adjusted under 35 U.S.C. 154(b) by 423 days.

(21) Appl. No.: 17/712,789

(22) Filed: Apr. 4, 2022

(65) Prior Publication Data

US 2023/0056440 A1 Feb. 23, 2023

Related U.S. Application Data

(63) Continuation of application No. PCT/CA2021/050469, filed on Apr. 8, 2021, which is
(Continued)

(51) Int. Cl.
*A61M 60/216* (2021.01)
*A61M 60/135* (2021.01)
(Continued)

(52) U.S. Cl.
CPC ........ *A61M 60/216* (2021.01); *A61M 60/135* (2021.01); *A61M 60/414* (2021.01); *A61M 60/806* (2021.01); *A61M 60/865* (2021.01)

(58) Field of Classification Search
CPC .............. A61M 60/216; A61M 60/806; A61M 60/414; A61M 60/135; A61M 60/865
(Continued)

(56) References Cited

U.S. PATENT DOCUMENTS 4,625,712 A 12/1986 Wampler
4,646,719 A 3/1987 Neuman et al.
(Continued)

FOREIGN PATENT DOCUMENTS

CA 2701810 A1 4/2009
CA 3014105 A1 8/2017
(Continued)

OTHER PUBLICATIONS

Rhee and Blackshear, "Left Ventricular Assist Using a Jet Pump," ASAIO Trans., July-Sep. 1990, 36(3):M515-M518.
(Continued)

*Primary Examiner* — Michael J Lau

(57) ABSTRACT

Mammalian body implantable fluid flow influencing device, comprising a modular impeller having: An impeller hub module dimensioned and shaped to be deliverable to a delivery site within a conduit of a conduit system of the mammalian body via a catheter. An impeller vane module having at least a portion of an impeller vane; having, with respect to the impeller hub module, an assembled configuration in which the impeller vane module mates with the impeller hub module, and an unassembled configuration, in which the impeller vane module is unmated with the impeller hub module and being dimensioned and shaped to be deliverable to the delivery site via the catheter when in the unassembled configuration. The modular impeller being formed when the impeller vane module is retained in its assembled configuration, and dimensioned and shaped to be operable within at least one conduit of the conduit system. Method of implantation disclosed.

30 Claims, 22 Drawing Sheets

Related U.S. Application Data a continuation of application No. PCT/IB2021/052465, filed on Mar. 25, 2021, which is a continuation-in-part of application No. 17/063,129, filed on Oct. 5, 2020, now abandoned, said application No. PCT/CA2021/050469 is a continuation-in-part of application No. 17/063,129, filed on Oct. 5, 2020, now abandoned, application No. 17/712,789 is a continuation-in-part of application No. PCT/CA2020/051677, filed on Dec. 5, 2020.

(60) Provisional application No. 63/109,846, filed on Nov. 4, 2020, provisional application No. 62/911,257, filed on Oct. 5, 2019.

(51) Int. Cl.
    *A61M 60/414* (2021.01)
    *A61M 60/806* (2021.01)
    *A61M 60/865* (2021.01)

(58) Field of Classification Search
    USPC .......................................................... 600/16
    See application file for complete search history.

(56) References Cited

U.S. PATENT DOCUMENTS

| | | |
|---|---|---|
| 4,753,221 A | 6/1988 | Kensey et al. |
| 4,957,504 A | 9/1990 | Chardack |
| 4,964,864 A | 10/1990 | Summers et al. |
| 5,112,349 A | 5/1992 | Summers et al. |
| 5,749,855 A | 5/1998 | Reitan |
| 5,888,241 A | 3/1999 | Jarvik |
| 5,957,672 A | 9/1999 | Aber |
| 6,015,272 A | 1/2000 | Antaki et al. |
| 6,050,987 A | 4/2000 | Rosenbaum |
| 6,176,848 B1 | 1/2001 | Rau et al. |
| 6,210,318 B1 | 4/2001 | Lederman |
| 6,245,007 B1 | 6/2001 | Bedingham et al. |
| 6,527,800 B1 | 3/2003 | McGuckin, Jr. et al. |
| 6,669,624 B2 | 12/2003 | Frazier |
| 6,827,733 B2 | 12/2004 | Boneau |
| 6,942,611 B2 | 9/2005 | Siess |
| 6,981,942 B2 | 1/2006 | Khaw et al. |
| 7,022,100 B1 | 4/2006 | Aboul-Hosn et al. |
| 7,027,875 B2 | 4/2006 | Siess et al. |
| 7,070,555 B2 | 7/2006 | Siess |
| 7,144,364 B2 | 12/2006 | Barbut et al. |
| 7,393,181 B2 | 7/2008 | McBride et al. |
| 7,479,102 B2 | 1/2009 | Jarvik |
| 7,762,977 B2 | 7/2010 | Porter et al. |
| 7,841,976 B2 | 11/2010 | McBride et al. |
| 7,909,862 B2 | 3/2011 | Garrison et al. |
| 7,914,436 B1 | 3/2011 | Kung |
| 7,918,880 B2 | 4/2011 | Austin |
| 7,993,259 B2 | 8/2011 | Kang et al. |
| 7,998,190 B2 | 8/2011 | Gharib et al. |
| 7,998,954 B2 | 8/2011 | Otsubo et al. |
| 8,012,079 B2 | 9/2011 | Delgado, III |
| 8,075,472 B2 | 12/2011 | Zilbershlag et al. |
| 8,157,758 B2 | 4/2012 | Pecor et al. |
| 8,308,798 B2 | 11/2012 | Pintor et al. |
| 8,333,687 B2 | 12/2012 | Farnan et al. |
| 8,343,029 B2 | 1/2013 | Farnan et al. |
| 8,394,010 B2 | 3/2013 | Farnan |
| 8,439,859 B2 | 5/2013 | Pfeffer et al. |
| 8,449,443 B2 | 5/2013 | Rodefeld et al. |
| 8,489,190 B2 | 7/2013 | Pfeffer et al. |
| 8,579,858 B2 | 11/2013 | Reitan et al. |
| 8,585,572 B2 | 11/2013 | Mehmanesh |
| 8,617,239 B2 | 12/2013 | Reitan |
| 8,690,749 B1 | 4/2014 | Nunez |
| 8,727,959 B2 | 5/2014 | Reitan et al. |
| 8,734,331 B2 | 5/2014 | Evans et al. |
| 8,777,832 B1 | 7/2014 | Wang et al. |
| 8,784,291 B2 | 7/2014 | Farnan et al. |
| 8,814,933 B2 | 8/2014 | Siess |
| 8,821,366 B2 | 9/2014 | Farnan et al. |
| 8,944,748 B2 | 2/2015 | Liebing |
| 9,022,916 B2 | 5/2015 | Farnan et al. |
| 9,211,367 B2 | 12/2015 | Farnan et al. |
| 9,216,298 B2 | 12/2015 | Jacobson |
| 9,217,442 B2 | 12/2015 | Wiessler et al. |
| 9,314,559 B2 | 4/2016 | Smith et al. |
| 9,328,741 B2 | 5/2016 | Liebing |
| 9,339,597 B2 | 5/2016 | Khanal et al. |
| 9,358,330 B2 | 6/2016 | Schumacher |
| 9,375,580 B2 | 6/2016 | Bonner et al. |
| 9,416,791 B2 | 8/2016 | Toellner |
| 9,421,311 B2 | 8/2016 | Tanner et al. |
| 9,446,179 B2 | 9/2016 | Keenan et al. |
| 9,572,915 B2 | 2/2017 | Heuring et al. |
| 9,616,159 B2 | 4/2017 | Anderson et al. |
| 9,744,281 B2 | 8/2017 | Siegenthaler |
| 9,808,633 B2 | 11/2017 | Bonner et al. |
| 9,861,729 B2 | 1/2018 | Morello et al. |
| 9,872,947 B2 | 1/2018 | Keenan et al. |
| 9,878,079 B2 | 1/2018 | Pfeffer et al. |
| D811,588 S | 2/2018 | Kaiser et al. |
| 9,889,242 B2 | 2/2018 | Pfeffer et al. |
| D826,401 S | 8/2018 | Epple |
| 10,039,873 B2 | 8/2018 | Siegenthaler |
| 10,119,550 B2 | 11/2018 | Bredenbreuker et al. |
| 10,137,232 B2 | 11/2018 | Yomtov et al. |
| 10,143,788 B2 | 12/2018 | Rudser et al. |
| 10,179,197 B2 | 1/2019 | Kaiser et al. |
| 10,183,104 B2 | 1/2019 | Anderson et al. |
| 10,279,094 B2 | 5/2019 | Williams et al. |
| 10,293,090 B2 | 5/2019 | Bonde et al. |
| D855,175 S | 7/2019 | Epple |
| 10,363,349 B2 * | 7/2019 | Muller .................. A61M 60/17 |
| 10,413,648 B2 | 9/2019 | Delgado, III |
| 10,426,880 B2 | 10/2019 | Kushwaha et al. |
| 10,443,738 B2 | 10/2019 | Durst et al. |
| 10,449,276 B2 | 10/2019 | Pfeffer et al. |
| 10,478,538 B2 | 11/2019 | Scheckel et al. |
| 10,478,539 B2 | 11/2019 | Pfeffer et al. |
| 10,500,323 B2 | 12/2019 | Heuring et al. |
| 10,596,019 B2 | 3/2020 | Melsheimer et al. |
| 10,722,631 B2 | 7/2020 | Salahieh et al. |
| 10,799,624 B2 | 10/2020 | Pfeffer et al. |
| 10,898,626 B2 | 1/2021 | Siegenthaler |
| 10,926,013 B2 | 2/2021 | Schumacher et al. |
| 10,980,927 B2 | 4/2021 | Pfeffer et al. |
| 11,103,690 B2 | 8/2021 | Epple |
| 11,123,539 B2 | 9/2021 | Pfeffer et al. |
| 11,129,978 B2 | 9/2021 | Pfeffer et al. |
| 11,154,704 B2 | 10/2021 | Farnan et al. |
| 11,167,124 B2 | 11/2021 | Pfeffer et al. |
| 11,179,557 B2 | 11/2021 | Georges et al. |
| 11,202,902 B2 | 12/2021 | Najar |
| 11,235,137 B2 | 2/2022 | Salys |
| 11,235,138 B2 | 2/2022 | Gross-Hardt et al. |
| 11,241,569 B2 | 2/2022 | Delgado, III |
| 11,318,017 B2 | 5/2022 | Besselink |
| 11,324,940 B2 | 5/2022 | Earles et al. |
| 11,331,465 B2 | 5/2022 | Epple |
| 11,351,359 B2 | 6/2022 | Clifton et al. |
| 11,452,859 B2 | 9/2022 | Earles et al. |
| 11,471,665 B2 | 10/2022 | Clifton et al. |
| 11,534,593 B2 * | 12/2022 | Franano .............. A61M 60/232 |
| 11,690,997 B2 | 7/2023 | Georges et al. |
| 12,053,623 B2 | 8/2024 | Georges et al. |
| 12,161,853 B2 | 12/2024 | Crête et al. |
| 2005/0220636 A1 | 10/2005 | Henein et al. |
| 2006/0036127 A1 | 2/2006 | Delgado |
| 2007/0156006 A1 | 7/2007 | Smith et al. |
| 2007/0213690 A1 | 9/2007 | Phillips et al. |
| 2007/0250120 A1 | 10/2007 | Flach et al. |
| 2008/0004652 A1 | 1/2008 | Abboud et al. |
| 2008/0132748 A1 | 6/2008 | Shifflette |
| 2008/0154328 A1 | 6/2008 | Thompson et al. |
| 2009/0112312 A1 | 4/2009 | LaRose et al. |

(56) References Cited

U.S. PATENT DOCUMENTS

| | | | |
|---|---|---|---|
| 2009/0149950 A1* | 6/2009 | Wampler | A61M 60/178 623/3.13 |
| 2009/0247945 A1 | 10/2009 | Levit et al. | |
| 2010/0249489 A1 | 9/2010 | Jarvik | |
| 2010/0249491 A1 | 9/2010 | Farnan et al. | |
| 2010/0268017 A1 | 10/2010 | Siess | |
| 2011/0004046 A1* | 1/2011 | Campbell | A61M 60/422 600/16 |
| 2011/0106120 A1 | 5/2011 | Haselby et al. | |
| 2012/0041255 A1 | 2/2012 | Delgado, III | |
| 2012/0046515 A1 | 2/2012 | Woo et al. | |
| 2012/0053670 A1 | 3/2012 | Purdy | |
| 2012/0101455 A1 | 4/2012 | Liebing | |
| 2012/0149229 A1 | 6/2012 | Kearsley et al. | |
| 2012/0172654 A1 | 7/2012 | Bates | |
| 2012/0172655 A1 | 7/2012 | Campbell et al. | |
| 2012/0178985 A1 | 7/2012 | Walters et al. | |
| 2012/0178986 A1 | 7/2012 | Campbell et al. | |
| 2012/0203328 A1 | 8/2012 | Yribarren | |
| 2012/0226309 A1 | 9/2012 | Jönsson | |
| 2012/0253387 A1 | 10/2012 | Teichman et al. | |
| 2012/0310036 A1 | 12/2012 | Peters et al. | |
| 2013/0138205 A1 | 5/2013 | Kushwaha et al. | |
| 2013/0204362 A1* | 8/2013 | Toellner | A61M 60/808 623/3.13 |
| 2013/0253344 A1 | 9/2013 | Griswold et al. | |
| 2013/0253347 A1 | 9/2013 | Griswold et al. | |
| 2014/0012065 A1* | 1/2014 | Fitzgerald | A61M 60/859 600/16 |
| 2014/0031607 A1 | 1/2014 | Zilbershlag et al. | |
| 2014/0066979 A1 | 3/2014 | Jonsson | |
| 2014/0275726 A1 | 9/2014 | Zeng | |
| 2015/0250935 A1 | 9/2015 | Anderson et al. | |
| 2015/0290372 A1* | 10/2015 | Muller | A61M 60/554 600/16 |
| 2015/0306291 A1* | 10/2015 | Bonde | A61M 60/865 600/16 |
| 2015/0320991 A1 | 11/2015 | Sabin et al. | |
| 2016/0022890 A1 | 1/2016 | Schwammenthal et al. | |
| 2016/0089482 A1 | 3/2016 | Siegenthaler | |
| 2016/0206798 A1 | 7/2016 | Williams et al. | |
| 2016/0256620 A1 | 9/2016 | Scheckel et al. | |
| 2016/0279310 A1 | 9/2016 | Scheckel et al. | |
| 2017/0035954 A1* | 2/2017 | Muller | A61M 60/824 |
| 2017/0087288 A1 | 3/2017 | Gross-Hardt et al. | |
| 2017/0119945 A1 | 5/2017 | Neumann | |
| 2017/0173242 A1 | 6/2017 | Anderson et al. | |
| 2017/0274128 A1 | 9/2017 | Tamburino et al. | |
| 2017/0340789 A1 | 11/2017 | Bonde et al. | |
| 2017/0340877 A1 | 11/2017 | Ollivier | |
| 2018/0110909 A1 | 4/2018 | LaRose et al. | |
| 2018/0126130 A1* | 5/2018 | Nitzan | A61B 5/418 |
| 2018/0193543 A1 | 7/2018 | Sun | |
| 2018/0214141 A1 | 8/2018 | Mendez | |
| 2018/0243551 A1 | 8/2018 | Nagaoka et al. | |
| 2018/0250457 A1 | 9/2018 | Morello et al. | |
| 2019/0046703 A1* | 2/2019 | Shambaugh | F04D 29/061 |
| 2019/0105437 A1* | 4/2019 | Siess | A61M 60/216 |
| 2019/0126014 A1 | 5/2019 | Kapur et al. | |
| 2019/0358382 A1 | 11/2019 | Delgado, III | |
| 2020/0023109 A1 | 1/2020 | Epple | |
| 2020/0023158 A1 | 1/2020 | Epple | |
| 2020/0054806 A1 | 2/2020 | Sun | |
| 2020/0261633 A1 | 8/2020 | Spanier et al. | |
| 2020/0316277 A1 | 10/2020 | Delgado, III | |
| 2020/0330665 A1 | 10/2020 | Josephy et al. | |
| 2020/0405926 A1 | 12/2020 | Alexander et al. | |
| 2021/0008261 A1 | 1/2021 | Calomeni et al. | |
| 2021/0008263 A1 | 1/2021 | Leonhardt | |
| 2021/0077687 A1 | 3/2021 | Leonhardt | |
| 2021/0106808 A1 | 4/2021 | Siegenthaler | |
| 2021/0170081 A1 | 6/2021 | Kanz | |
| 2021/0177425 A1* | 6/2021 | Kapur | A61M 60/531 |
| 2021/0260360 A1 | 8/2021 | Georges et al. | |
| 2022/0080183 A1 | 3/2022 | Earles et al. | |
| 2022/0080184 A1 | 3/2022 | Clifton et al. | |
| 2022/0134082 A1 | 5/2022 | Pfeffer et al. | |
| 2022/0226634 A1 | 7/2022 | Gross-Hardt et al. | |
| 2022/0249830 A1 | 8/2022 | Kanz | |
| 2022/0257920 A1 | 8/2022 | Earles et al. | |
| 2022/0296852 A1 | 9/2022 | Georges | |
| 2022/0296880 A1 | 9/2022 | Clifton et al. | |
| 2022/0323744 A1 | 10/2022 | Georges et al. | |
| 2022/0331576 A1 | 10/2022 | Leonhardt | |
| 2023/0137466 A1 | 5/2023 | Georges et al. | |
| 2023/0293880 A1 | 9/2023 | Georges et al. | |
| 2024/0090882 A1 | 3/2024 | Georges et al. | |
| 2024/0198078 A1 | 6/2024 | Crête et al. | |
| 2024/0342460 A1 | 10/2024 | Georges et al. | |

FOREIGN PATENT DOCUMENTS

| | | |
|---|---|---|
| CA | 3054771 A1 | 9/2018 |
| CN | 106456857 B | 11/2018 |
| CN | 109069716 A | 12/2018 |
| CN | 112870547 A | 6/2021 |
| CN | 110049792 B | 1/2022 |
| DE | 19613565 C1 | 7/1997 |
| DE | 102004054714 A1 | 5/2006 |
| DE | 202009018416 U1 | 8/2011 |
| EP | 2860849 A1 | 4/2015 |
| EP | 3456367 A1 | 3/2019 |
| EP | 3539584 A1 | 9/2019 |
| EP | 2745805 B2 | 5/2022 |
| WO | WO-0227225 A1 | 4/2002 |
| WO | WO-03103745 A2 | 12/2003 |
| WO | WO-2008017289 A2 | 2/2008 |
| WO | WO-2008027366 A2 | 3/2008 |
| WO | WO-2010133567 A1 | 11/2010 |
| WO | WO-2012094641 A2 | 7/2012 |
| WO | WO-2013062859 A1 | 5/2013 |
| WO | WO-2013093058 A1 | 6/2013 |
| WO | WO-2014070472 A1 | 5/2014 |
| WO | WO-2015109028 A1 | 7/2015 |
| WO | WO-2015148821 A1 | 10/2015 |
| WO | WO-2015177793 A2 | 11/2015 |
| WO | WO-2016185473 A1 | 11/2016 |
| WO | WO-2017185082 A1 | 10/2017 |
| WO | WO-2017217946 A1 | 12/2017 |
| WO | WO-2018096531 A1 | 5/2018 |
| WO | WO-2018129177 A1 | 7/2018 |
| WO | WO-2018158635 A1 | 9/2018 |
| WO | WO-2018226991 A1 | 12/2018 |
| WO | WO-2019057636 A1 | 3/2019 |
| WO | WO-2019083989 A1 | 5/2019 |
| WO | WO-2019094963 A1 | 5/2019 |
| WO | WO-2019152875 A1 | 8/2019 |
| WO | WO-2019183247 A1 | 9/2019 |
| WO | WO-2019191851 A1 | 10/2019 |
| WO | WO-2020036886 A1 | 2/2020 |
| WO | WO-2020198765 A2 | 10/2020 |
| WO | WO-2021062565 A2 | 4/2021 |
| WO | WO-2021062566 A1 | 4/2021 |
| WO | WO-2021117021 A1 | 6/2021 |
| WO | WO-2021138673 A1 | 7/2021 |
| WO | WO-2021234638 A1 | 11/2021 |
| WO | WO-2022094690 A1 | 5/2022 |
| WO | WO-2022096941 A1 | 5/2022 |
| WO | WO-2023178431 A1 | 9/2023 |
| WO | WO-2024092349 A1 | 5/2024 |
| WO | WO-2024229567 A1 | 11/2024 |
| WO | WO-2025019957 A1 | 1/2025 |

OTHER PUBLICATIONS

International Preliminary Report on Patentability issued in PCT/CA2019/050421, dated Oct. 6, 2020, 9 pages.

International Preliminary Report on Patentability issued in PCT/CA2020/051673, dated Apr. 5, 2021, 7 pages.

International Preliminary Report on Patentability issued in PCT/CA2020/051677, dated Apr. 5, 2021, 7 pages.

(56) References Cited

OTHER PUBLICATIONS

International Preliminary Report on Patentability issued in PCT/ZA2020/050022, dated Sep. 28, 2021, 5 pages.
International Search Report and Written Opinion for PCT/ZA2020/050022, dated Sep. 24, 2020, 6 pages.
International Search Report and Written Opinion issued in PCT/CA2019/050421 dated Jul. 8, 2019, 12 pages.
International Search Report and Written Opinion issued in PCT/CA2020/051673 dated Mar. 26, 2021, 12 pages.
International Search Report and Written Opinion issued in PCT/CA2020/051677, dated Mar. 15, 2021, 11 pages.
International Search Report and Written Opinion issued in PCT/CA2021/050469 dated Jul. 28, 2021, 10 pages.
International Search Report and Written Opinion issued in PCT/IB2020/061913 dated Mar. 19, 2021, 11 pages.
International Search Report and Written Opinion issued in PCT/IB2021/052925 dated Jul. 28, 2021, 14 pages.
International Search Report and Written Opinion issued in PCT/IB2021/054395 dated Aug. 12, 2021, 9 pages.
International Search Report and Written Opinion issued in PCT/US2021/012083 dated Mar. 31, 2021, 7 pages.
Notice of Allowance issued in U.S. Appl. No. 17/047,598 dated May 3, 2021, 7 pages.
Supplemental International Search Report issued in PCT/ZA2020/050022, dated Jul. 13, 2021, 8 pages.
Notice of Allowance for U.S. Appl. No. 17/752,378 dated Feb. 16, 2023, 12 pages.
Extended European Search Report for European Application No. EP21736214.4 dated Jan. 3, 2024, 9 pages.
Extended European Search Report for European Application No. EP23166411.1 dated Oct. 6, 2023, 10 pages.
International Preliminary Report on Patentability issued in PCT/CA2023/050378, dated Sep. 24, 2024, 5 pages.
International Preliminary Report on Patentability issued in PCT/US2021/012083, dated Jul. 14, 2022, 7 pages.
International Search Report and Written Opinion for International Application No. PCT/CA2023/050378 dated Jun. 9, 2023, 8 pages.
International Search Report and Written Opinion for International Application No. PCT/CA2023/051450 dated Jan. 16, 2024, 9 pages.
International Search Report and Written Opinion for PCT Application No. PCT/CA2024/050620 mailed Jul. 24, 2024, 8 pages.
International Search Report and Written Opinion for PCT Application No. PCT/CA2024/051004 mailed Oct. 21, 2024, 12 pages.
Lo Coco, V. et al. "Right ventricular failure after left ventricular assistance device implantation: a review of the literature," J. Thorac. Dis., Feb. 2021, 13(2):1256-1269.
Rogers, T. et al. NIH, National Heart, Lung, and Blood Institute "First in Man Testing of a Dedicated Closure Device for Transcaval Access for Transcatheter Aortic Valve Replacement," NCT03432494, Publication Date Unknown, 16 pages.

* cited by examiner

MAMMALIAN BODY IMPLANTABLE FLUID FLOW INFLUENCING DEVICE

CROSS-REFERENCE

The present application is a continuation of International Patent Application No. PCT/CA2021/050469, filed Apr. 8, 2021 (pending) (the '469 PCT) and is a continuation-in-part of International Patent Application No. PCT/CA2020/051677, filed Dec. 5, 2020 (pending) (the '677 PCT). The '469 PCT is a continuation of International Patent Application No. PCT/IB2021/052465, filed Mar. 25, 2021 (expired) (the '465 PCT), which claims priority to and the benefit of U.S. Provisional Application No. 63/109,846, filed Nov. 4, 2020 (the '846 Provisional). The '465 PCT is also a continuation-in-part of U.S. patent application Ser. No. 17/063,129, filed Oct. 5, 2020 (abandoned) (the '129 application), which claims priority to and the benefit of U.S. Provisional Application No. 62/911,257, filed Oct. 5, 2019 (the '257 Provisional). The '469 PCT claims priority to and the benefit of the '846 Provisional, and is a continuation-in-part of the '129 application. The '677 PCT claims priority to and the benefit of the '257 Provisional. The contents of each one of the foregoing applications are incorporated herein by reference in their entirety for all purposes.

FIELD

The present technology relates to mammalian body implantable fluid flow influencing devices.

BACKGROUND

General

Fluid carrying conduits in patients, such as blood vessels or other conduits near the heart, liver or kidneys that carry fluids other than blood (e.g., urine, lymph, etc.), may require fluid flow influencing (e.g., an increase in fluid flow rate, a decrease in fluid flow rate, a stoppage of fluid flow, a diversion of fluid flow, etc.) in various medical situations.

Heart failure is an example of a common such situation. In patients with heart failure, their heart becomes unable to pump enough blood to meet their body's needs for blood and oxygen.

Heart Failure

Heart failure is a disease affecting upwards of 6 million Americans and 26 million people worldwide at any given time. There is no cure. For those suffering from heart failure, their ability to function in everyday life and their overall quality of life steadily and inevitably decline. There may be times of rapid deterioration. Even with the best of medical care, heart failure sufferers' symptoms will slowly, inevitably progress. They will rapidly become limited in their activities. At some point in time, they will experience increasing symptoms of the disease even at rest and under optimal medical therapy. People with end-stage heart failure disease currently have a 2-year estimated chance of survival of only 20%.

To try to improve this somber forecast of the probable course and outcome of the disease, multiple strategies for caring for people having heart disease have been developed. Such strategies include both short-term mechanical patient support options, as well as longer-term patient support options. Unfortunately, none of the options currently available are optimal.

Open Surgery Vs. Minimally Invasive Surgery

Prior to review of the current conventional treatment possibilities, it should be noted that all such treatments are surgical in nature. They may be carried out on a patient suffering from the disease either via "open surgery" (i.e., the traditional surgical method of the cutting of skin and tissues so that the surgeon has a full view of the structures or organs involved) or via "minimally invasive surgery" (i.e., newer surgical techniques that do not require large incisions). Examples of minimally invasive surgical techniques are percutaneous transcatheter techniques, in which a catheter (e.g., a relatively long flexible tube) is inserted into the patient's body and the intervention is performed through the lumen (i.e., the hollow cavity) of the catheter at a site distal to (e.g., away from) the catheter insertion site. As compared with open surgical techniques, transcatheter techniques generally are lower risk to the patient, shorter in time for the surgeon to perform, and have shorter patient recuperation times. They are usually preferred by patients.

Heart Transplants

One current treatment possibility for heart disease is a heart transplant. Heart transplantation involves the removal of a patient's diseased heart and its replacement with a healthier heart from a heart donor. There are, however, an extremely limited number of donor hearts available. In North America for example, only about 3,000 donor hearts are available each year. So, heart transplantation is not an option which is generally available to patients, as the number of donor hearts is far less than the number of sufferers of the disease. Further, heart transplantation obviously requires very invasive open surgery. It carries additional significant risks, including (but in no way limited to) transplant coronary artery disease and life-long suppression of the recipient's immune system. For all of these reasons, heart transplantation is in most cases limited to younger patients, and therefore younger patients are prioritized on heart transplant lists.

Artificial Hearts

Another current treatment possibility for heart disease is through the removal of a patient's diseased heart and its replacement with an artificial heart device (typically known as a "total artificial heart"). While the number of total artificial hearts is not limited (as is the case with donor human hearts) as they are manufactured devices, at the moment their use is limited to being only temporary. No total artificial heart is available for permanent implantation. Thus, total artificial hearts are used in patients who are in the end-stages of heart disease, but for whom no donor heart is yet available. Their use is quite limited, as the number of donor hearts is limited. In addition, implantation of a total artificial heart still requires very invasive open surgery, and carries risks as noted above. There are very few total artificial heart products currently available for use in patients. One product is the SynCardia™ Temporary Artificial Heart. Another potential product, which is still in development, is the Carmat™ artificial heart.

Ventricular Assist Devices (Open Surgical Implantation)

A third current treatment possibility for heart disease, and the most common, is through the implantation and use of what is known as a "Ventricular Assist Device" (commonly abbreviated to and referred to as a 'VAD'). A VAD is a mechanical pump that is surgically implanted within a patient to help a weakened heart pump blood. Unlike a total artificial heart, a VAD does not replace a patient's own heart, instead it helps the patient's native heart pump blood. VADs may be used to help the left side of a patient's heart, in which case they are known as LVADs. Or, they may be used to help the right side of a patient's heart, in which case they are known as RVADs. LVADs are far more commonly used. Currently, VADs may either be used as a bridge until a heart transplant can be performed (as is the case with total artificial hearts) or they may be used long term in patients whose condition makes it impossible to receive a heart transplant or who require immediate long-term support. There are different types and configurations of VADs, some of which will be discussed below.

Common to almost all currently available VADs is that their implantation requires open surgery, and carries the downsides and risks thereof noted above, and others. The complication rate and the mortality rate associated with the use of VADs are both significant. For example, patients are at risk of embolic stroke (e.g., a stroke caused by the blockage of a blood vessel due to a blood clot having formed), for amongst other reasons, the positioning of a VAD at the apex of the heart. Patients are also at risk of a cerebral (i.e., brain) or gastro-intestinal hemorrhage as most VADs pump blood continuously (as opposed to a normal heart, which pumps blood in pulses). This continuous pumping of blood causes the patient's blood vessels to become more fragile (and thus prone to hemorrhaging) and also causes a decrease in the patent's von Willebrand factor (which is a molecule in human blood that is part of the process to prevent and stop bleeding). Further, owing to the complexity of the VAD implantation surgery, VADs are only implanted in specialized centers. Indeed, the number one reason for patients refusing to undergo VAD implantation is the patient's fear of such invasive implantation surgery and the complications arising therefrom. For all of these reasons, although more than 250,000 heart disease suffers in North America alone could benefit from VAD implantation, there are less than 4,000 yearly VAD implants in the United States.

All of these generations of VADs described above that are currently in use (or previously had been used) require (or required) invasive classic open surgery (e.g., a median sternotomy or a less invasive mini-thoracotomy). During the implantation procedure, a VAD is surgically attached (e.g., sutured) to the heart while the main VAD body remains external to the patient's vasculature (e.g., heart and blood vessels). The pump inlet of the VAD is sutured to the left or right ventricle of the heart (depending on whether the VAD is an LVAD or an RVAD) and the outflow tubing from the VAD is sutured to the aorta (in the case of an LVAD) or the pulmonary artery (in the case of an RVAD).

Ventricular Assist Devices (Minimally Invasive Surgical Implantation)

As was described above, however, patients prefer minimally invasive percutaneous transcatheter interventions to open surgery. And thus, the most recent efforts in the development of mechanical support strategies for people with heart disease have been made towards the development of pumps that do not require open surgery, but rather could be implantable transcatheter.

Currently, the only commercial product that can be implanted percutaneously transcatheter is the Impella™ family of micro-pump devices from Abiomed™. An Impella device has a single micro axial pump (e.g., having an impeller) with a cannula (e.g., a small tube-like structure). The device is implanted within the left ventricle (in the case of an LVAD) or right ventricle (in the case of an RVAD) of the heart so as to cross the aortic valve (in the case of an LVAD) or tricuspid and pulmonary valve (in the case of an RVAD). The inlet of the pump is within the ventricle or within the vessels that discharge fluid into the ventricle and the outlet of the pump is outside of the heart, in the aorta (in the case of an LVAD) and in the pulmonary artery (in the case of an RVAD). As the pump impeller turns, blood is drawn into the device through the pump inlet. The blood then travels under pressure having been imparted by the pump through the cannula and exits the device through the pump outlet in the aorta or pulmonary artery (as the case may be). In this manner, the VAD provides pumping assistance to the ventricle of the heart.

An Impella device is implanted via a percutaneous procedure. In a percutaneous procedure access to the patient's internal organs is made via needle-puncture of the skin (e.g., via the well-known conventional Seldinger technique). Typically, in such procedures, the needle-puncture site is relatively remote from the actual internal organs that the surgeon will be operating on. For example, although it is the heart that a surgeon will be operating on, the initial needle puncture of the skin takes place in the patient's groin area so that the surgeon can access the patient's vasculature through the femoral vessels. Once access is obtained, the surgeon can advance the necessary tools to conduct the surgical procedure through the patient's vasculature to their heart. The surgeon then conducts the procedure on the heart, usually via wires extending from the tools, travelling through the patient's vasculature and outside of the patient's body via the access opening that the surgeon had previously made. Once the procedure has been completed, the surgeon removes the tools from the patient's vasculature in the same manner. In such procedures, access via the femoral artery (in the patient's groin area) or the axillary artery (about the patient's clavicle) are more common.

One difficulty that arises with respect to such percutaneous procedures and devices, such an Impella device, is that the size of the device is significantly limited because of the remote peripheral insertion location of the device (through femoral or axillary artery, as the case may be). I.e., the size of the structures that will travel through the patient's blood vessels is limited to being only slightly larger than those vessels themselves, as those vessels can only stretch a limited amount before they will become damaged. Additionally, peripheral vascular disease, which is very common in older patients, further reduces the size and compliance of vessels due to atheromatous plaque build-up and calcification. In the context of an Impella device, what this means is that the actual physical size of the pump (including the motor and the impeller) is limited since the pump must travel through the patient's blood vessels to the patient's heart.

This, in turn, limits the actual physical size of the cannula of the pump through which the pumped blood will flow. Thus, in order for the Impella device pump to provide a sufficient volume of blood flow through the cannula to adequately assist the patient's heart, the impeller of the pump will have to rotate at a very high speed. (Generally, the higher the rotation speed of the impeller of a fixed diameter, the more blood the pump will pump.) This high impeller rotation speed can be problematic, however. High impeller rotation speed generates substantial shear stress forces on the blood elements being pumped, leading to known detrimental phenomena such as platelet activation, von Willebrand factor multimer destruction, destruction of red blood cells (hemolysis) and thrombus formation. All of which can lead to embolic strokes or pump thrombosis, as described above.

Expandable Impellers

In view of these potential issues with high impeller rotation speed pumps, other solutions have been sought. Setting aside for the moment the limitation on size of the pump (and thus the diameter of the impeller) discussed above, generally the volume of fluid pumped by an impeller can also be increased by having an impeller of greater diameter (in addition to increasing the impeller rotation speed as discussed above). Thus, if one were to limit the speed of rotation of an impeller to a speed whereat the sheer stress on the blood (the pumped fluid) is at an acceptable level (to reduce the risk of the detrimental phenomena described above), given a desired volumetric flow rate for the pump, a particular impeller diameter (amongst other impeller design considerations) to achieve that flow rate at that rotation speed can be calculated.

From all of this it follows that a potential solution to this situation would be to have an impeller that was of a smaller diameter when being delivered through the vascular system of the patient and was of a larger diameter when operating at the implantation site. Hence, expandable impeller pumps for use in this situation were conceived of.

As background on expandable impeller pumps, U.S. Pat. No. 7,393,181 (McBride et al.), issued Jul. 1, 2008, entitled "Expandable Impeller Pump" (hereinafter "McBride et al.") describes "An impeller . . . comprises a hub, and at least one blade supported by the hub. The impeller has a deployed configuration in which the blade extends away from the hub, and a stored configuration in which the impeller is radially compressed, for example by folding the blade . . . " (Abstract, McBride et al.). For ease of understanding this concept, FIGS. 1A, 1B, 2, 3A and 3B of McBride et al. are reproduced herein as FIGS. 1A, 1B, 2, 3A, 3B (respectively). In discussing these figures, McBride et al. provides: "FIG. 1A shows an impeller in a deployed configuration, the impeller comprising a hub 10 and blades such as blade 12. The impeller has a radius R1, as measured from the central long axis of the hub to the outermost blade tip . . . . FIG. 1B shows the impeller in a stored configuration, with blade 12 folded or otherwise deformed towards the hub 10. The radius R2 is less than the radius R1 shown in FIG. 1A. An impeller according to an embodiment of the present invention has flexible blades that can be folded such that the maximum diameter of the impeller in the folded state is approximately half or less than half the diameter of the impeller in the operating state. Referring to FIGS. 1A and 1B, this corresponds to R2≈≤(R½) . . . . FIG. 2 is a schematic illustrating deployment of the impeller. The impeller has hub 20 and blades such as 22, and is retained in the stored configuration by storage sleeve 24. A rotating shaft 30 is used to drive the impeller. The figure also shows a guide wire 28 within the rotating shaft, which can be used to position the impeller, and also to help push the impeller out of the storage sleeve . . . . An impeller in the stored configuration can be stored in a cylindrical cavity formed by storage sleeve 24 of diameter approximately equal to or less than half the diameter of the fluid pipe 26 . . . . FIG. 3A further illustrates an impeller in a stored configuration, showing blades such as blade 34, and hub 30. The blades are kept folded against the hub by the storage sleeve 36. FIG. 3B shows the impeller pushed out of the storage sleeve and self-deployed" (McBride et al.; col. 5, line 57 to col. 6, line 53)

Returning to the discussion of the Impella devices, improved percutaneously transcatheterly-implantable VAD solutions have been conceived of. Such devices include devices developed by Magenta Medical™, by Second Heart Assist™, the Heartmate™ PHP by Abbott™ and others. These devices all have a common goal of overcoming the limitations of the Impella devices by using impellers that have the capability of being expanded in vivo as was generally discussed above. In this manner, a device can be implanted percutaneously transcatheterly with the pump impeller having vanes in a delivery (compact) configuration (the diameter of which being sufficiently small enough to be able to travel through a catheter extending within the patient's blood vessels, without causing damage). At the delivery site (or the implantation site, if the delivery site is not the implantation site) within the conduit system of the body, the impeller vanes then can be deployed (expanded) to yield an impeller having a larger diameter than the one it had with the delivery configuration. In this manner, in pumping the same amount of blood (i.e., having the same volumetric flow rate), the impeller of one of these devices can be operated at relatively lower speeds (as compared with the one of an Impella device—a non-expandable impeller), as the expandable impeller in its operating configuration has a relatively larger diameter than that of the Impella device impeller.

Expandable impellers of different constructions have been described in patent documents to date, some examples of which are provided hereinbelow:

An earlier approach in the design of such a device uses structural folding of the impeller vanes. Mechanical joints are provided to allow for this folding (and thus the compaction and expansion of the impeller vanes) to occur. Constructing the device in this manner may enable the device to provide more support for patients by generating more flow. This is because a larger expanded impeller will produce more flow at a fixed speed compared to a smaller non-expandable impeller.

U.S. Pat. No. 5,749,855 (Reitan), issued May 12, 1998, entitled "Catheter Pump" provides an example of such a design. Reitan teaches a device with impeller vanes rotatably or pivotably connected to a central hub. Thus, the vanes rotate or pivot from a compact (delivery, storage, etc.) configuration to an expanded (deployed, operational, etc.) configuration. The design of the Reitan device enables a relatively large change in impeller diameter between the compact and expanded configurations. Such a design thereby enables the implantation and operation of an impeller with a relatively large diameter and a lower rotational speed, thus enabling sufficient volumetric blood flow with reduced risk of negative impact on blood components. One major drawback of such as design, however, is that the design parameters of the impeller vanes (e.g., the impeller vane geometry) are very limited (as compared with non-expandable impeller vanes) as the impeller vanes need to be designed for the compact configuration, the expanded configuration, and the conversion therebetween. Impellers of a such a design therefore have a reduced hydraulic efficiency as compared with impellers that do not require such changes in configuration. Another drawback is that the mechanical joints on such devices (which enable the vanes to rotate or pivot) frequently represent a geometric discontinuity where blood stagnation can occur. Unfortunately, this elevates the risk of thromboembolism formation and negatively affects the clinical viability of devices of such a design. (This list of drawbacks is only exemplary.)

Another design approach for such devices to use inflatable mechanisms to convert the impeller vanes (and other structures of the device in some cases) from a compact configuration to an expanded configuration. U.S. Pat. No. 6,981,942 (Khaw et al.), issued Jan. 3, 2006, entitled "Temporary Blood Circulation Assist Device" and U.S. Pat. No. 8,814,933 (Siess), issued Aug. 26, 2014, entitled "Foldable Intravascularly Inserted Blood Pump" describe examples of devices employing such a mechanism. Unfortunately, the requirement for devices employing such a design to have a permanent supply of fluid to maintain the inflation pressure limits the portability of such device. Furthermore, the durability of an impeller encompassing complex and multiple mechanical joints (which is the case with devices of such a design) has not to date been proven in the clinical setting. Finally, in cases of thrombus formation, endothelialization and/or platelet aggregation on the joint surfaces, joint movement may be hindered and threaten device retrieval.

In yet another design approach, several patents teach using flexible components to enable compression of the impeller vanes to make possible their compact (stored, delivery, etc.) configuration. The vanes may then be deployed into their expanded configuration, for example, via extraction of the device from a cannula (e.g., McBride et al., referred to hereinabove) or through the use of various mechanisms (e.g., U.S. Pat. No. 9,217,442 (Wiessler et al.), issued Dec. 22, 2015, entitled "Pump or Rotary Cutter for Operation in a Fluid" and U.S. Pat. No. 9,416,791 (Toellner), issued Aug. 16, 2016, entitled "Fluid Pump Having a Radially Compressible Rotor"). While devices using these flexible component designs generally provide for simpler deployment and uniform geometries, the flexibility of the material can lead to flexing when the impeller is operating under high load, undesirably lowering hydraulic efficiency of the impeller. Additionally, most "foldable" devices are designed based on radial compression of the impeller vanes, which is only possible up to a certain limit depending on the properties of the material(s) of which they are made (e.g., solids can only be contracted to a certain extent by folding them). This compression limitation complexities the design as it impacts the diameter range of an impeller that can be employed (and such impeller design needs to be in accordance with clinical requirements of a peripheral implant). These geometrical compression requirements and limitations add restrictions with respect to the design of the impeller for hydraulic efficiency. Finally, there are also concerns over the durability of flexible impeller vanes as compared to with inflexible impeller vanes (e.g., made of hard plastics (such as polyether ether ketone (PEEK)) or metals (such as titanium)) currently used in approved devices. (Such inflexible impeller vanes thus do not suffer from these types of potential durability issues).

Giving the relatively frequent occurrence of heart failure described above and the likely severe consequences of the disease, further developments in devices used to the treat the disease are always being sought. Particular focus is on minimally invasive deceives, given the difficulties with the alternatives. At the present time, as the description of the history of the development of such devices set forth above shows, the current focus in technology development in this area is on improving the design of expandable impeller pumps to attempt to overcome their drawbacks. Improved VADs (and other similar body fluid flow influencing devices) would certainly be advantageous.

SUMMARY

It is thus an object of the present technology to ameliorate at least one of the inconveniences present in the prior art, be it one of those described hereinabove or another.

It is a further object of the present technology to provide an improved fluid flow influencing device (e.g., a VAD) at least as compared with a prior art device, be it one of those described herein above or another.

The present technology results (at least in part) from the developer's endeavors to overcome some of the drawbacks of expandable impeller pumps (including those described hereinabove), while simultaneously still providing their benefits (also described hereinabove). However, and without wishing to disparage in any way expandable impeller pumps, the approach of the developer was to take a "starting from scratch" impeller design, rather than simply start with a known expandable impeller pump design.

The result of such efforts is an impeller designed to have reduced diameter for delivery (and in some instances for storage, transport, and/or removal, etc.) and to have an increased diameter for operation, without requiring a conventional expandable impeller. The present technology achieves this result, in summary, by providing an impeller having an in vivo assemblable modular design. The modules making up the impeller are sequentially deliverable when unassembled to a delivery site within the mammalian body via a catheter having been percutaneously inserted into a conduit system (e.g., the vasculature) of the body. The modules are then assemblable at (or near) the delivery site to form the impeller. The assembled impeller is then operable at the delivery site (in which case the delivery site would be the implantation site) or is movable to an implantation site distinct from the delivery site and then operable at that location, as the case might be. (Typically, the latter would be the case when there would not be enough space at the implantation site to assemble the impeller (but there would be enough space to operate it), and there would be enough space at (or near) the delivery site to assemble the impeller). In this manner, an impeller having a particular operating diameter may be implantable within a body, notwithstanding the fact that that operating diameter exceeds the diameter of the conduits in the conduit system through which that impeller is to be delivered.

Thus, in one aspect, embodiments of the present technology provide a mammalian body implantable fluid flow influencing device. The device comprises a modular impeller. The modular impeller has an impeller hub module and at least one impeller vane module. The impeller hub module is dimensioned and shaped to be deliverable to a delivery site within a conduit of a conduit system of the mammalian body via a catheter. Each impeller vane module has at least a portion of an impeller vane. Each impeller vane module has, with respect to the impeller hub module, an assembled configuration in which the impeller vane module mates with the impeller hub module, and an unassembled configuration in which the impeller vane module is unmated with the impeller hub module. Each impeller vane module is dimensioned and shaped to be deliverable to the delivery site within the conduit of the conduit system of the mammalian body via the catheter when in the unassembled configuration. The modular impeller is formed when the impeller vane module is retained in its assembled configuration. The impeller is dimensioned and shaped to be operable within a conduit of the conduit system of the mammalian body, which, as was noted above, may in some cases be at the delivery site and in other cases may be at an implantation site distinct from the delivery site. Thus, the impeller is operable within at least one of the conduits of the conduit system of the mammalian body (to which it was delivered) and another conduit of the conduit system of the mammalian body (to which it may have been moved in vivo).

The modular impeller is dimensioned and shaped to be operable at/within the location of the body at which it is implanted and operated without causing material harm to the patient.

In the context of the present technology, the device is termed a "fluid flow influencing" device and not simply a "pump", as it is foreseen that it would be possible to operate the impeller of the device so as to increase the native volumetric flow rate (which, may, in some instances be zero), as in the case of a pump. It is also foreseen that it would be possible in some instances to operate the impeller of the device so as to decrease or divert the native volumetric flow rate within the conduit.

As was stated above, the modules of the modular impeller are dimensioned and shaped to be deliverable through the conduit system of the mammalian body via a catheter. Depending on the particular patient and the particular delivery site, the size of the catheter required may vary. For example, were the device to be implanted within a patient suffering from coronary artery disease with heart failure, their peripheral vasculature through which the catheter must pass may be partially blocked by peripheral artery disease and thus have reduced cross-sectional area as compared with that of a person not suffering from that disease. The surgeon would thus have to select the appropriately sized catheter and impeller modules (device) such that the catheter can pass through the minimum available cross-section of the blood vessels, to the delivery site, and the modules can be delivered (e.g., can themselves pass through) via the catheter to the delivery site.

As the skilled addressee would understand, the size of catheters for use in human beings is measured according to the French scale (Fr). Such catheters commonly vary in outer diameter between 3 Fr (1 mm) and 36 Fr (12 mm). (The Fr scale may be converted to millimetres by dividing the Fr by 3). So, for example, if it were determined that a 6 Fr catheter was to be used in a particular procedure, any components to be delivered through that catheter must be selected such that their dimensions and shapes will permit them to be delivered through a catheter of 6 Fr. Thus, in the present context, the impeller hub module and each of the impeller vane modules meet such a limitation.

In some embodiments, each one of the units to be implanted (e.g., an impeller hub module, an impeller vane module, a single implantable unit (as defined hereinbelow), etc.) has a minimum-bounding right circular cylinder. In the context of the present specification, a minimum bounding right circular cylinder is right circular cylinder whose axis is generally parallel to (including colinear with) a longitudinal axis of the object in question (e.g., an impeller vane module, an impeller hub module, etc. Each minimum-bounding right circular cylinder has a diameter, and each diameter is between 1 mm (3 Fr) and 12 mm (36 Fr) inclusive. In some embodiments, a difference between a largest one of the diameters and a smallest one of the diameters is at most 2 mm (6 Fr). As the minimum diameter of the catheter necessary will be defined by the largest diameter, as far as the design will allow, having the diameters of each of the units to be implanted close to one another is likely to be optimal in most embodiments.

In the context of the present technology, the impeller hub module is the module that has or forms most (if not all) of the impeller hub. (As would be understood by the skilled addressee, the hub is the central rotating part of the impeller to which torque is imparted and to which the vanes are attached). An impeller vane module is a module that has or forms most (if not all) of an impeller vane. (As would be understood by the skilled addressee, the vanes are the broad structures attached to the hub that impart motion to the fluid when the impeller rotates).

Depending on the particular design of an impeller hub module and impeller vane modules in a particular embodiment, a portion of the impeller hub may be part of the impeller vane module, and/or a portion of a vane (or vanes) may be present on an impeller hub module. Modules of the present technology do not lose their characterization as an impeller "hub" module merely because they do not form the entirety of the impeller hub. (E.g., the impeller vane modules may form a portion of the impeller hub, in some embodiments.) Similarly, modules of the present technology do not lose their characterization as an impeller "vane" module merely because they do not have the entirety of a vane. (E.g., the impeller hub module may have a portion of an impeller vane or vanes, in some embodiments).

Thus, in some embodiments, the impeller hub module has an outer surface that is shaped as a portion (or portions) of a curved side surface of a right circular cylinder. When each of the impeller vane modules is in its assembled configuration, the bases of the of the impeller vane modules have a surface shaped to align flush with the outer surface of the impeller hub module, and to complete the curved side surface of the right circular cylinder. Thus, in such embodiments at least part of the bases of the impeller vane modules will form part of the impeller hub when the impeller is fully assembled and operable.

In some embodiments, each of the impeller vane modules has a center of mass. When each of the impeller vane models is in its assembled configuration: (i) The centers of mass of the impeller vane modules are all equally angularly spaced around an axis of rotation of the impeller hub module in a plane perpendicular to the axis of rotation. (ii) The centers of mass of the impeller vane modules are equally radially distant from the axis of rotation of the impeller hub module in the plane. The purpose of such a design may be to assist in mass balancing of the assembled impeller.

Embodiments wherein each one of the impeller vane modules has an entirety of its impeller vane, are within the scope of the present technology as well.

In the art, and as used in the context of the present specification, the terms "vane" and "blade" are synonymous when referring parts of an impeller. For purposes of consistency, the present specification has been drafted entirely using the term "vane", but no distinction between that term and the term "blade" is intended thereby.

As was noted above, each impeller vane module has an assembled configuration and an unassembled configuration with respect to the impeller hub module. In the assembled configuration, the impeller vane module mates with the impeller hub module. In the present context, the term "mates" includes being correctly positioned one with respect to the other such that a portion of an operative impeller is formed. It is thus foreseen that in most (but not all) embodiments, there will be only one position of an impeller vane module with respect to the impeller hub module when the former is in the assembled configuration. In the unassembled configuration, the impeller module vane module is unmated with the impeller hub module. In the present context, the term "unmated" includes being positioned one with respect to the other such that no portion of an operative impeller is formed. It is thus foreseen that in most (but not all) embodiments, there will be a large number of positions which an impeller vane module may be in with respect to an impeller hub module when the former is in the unassembled configuration.

The modular impeller is formed when each of the impeller vane modules is retained in its assembled configuration. No particular means of retention is required. Any means of retention not incompatible with the delivery, assembly, operation, and removal of the modular impeller, nor incompatible with its use inside a living body, is within the scope of the present technology. Specific examples of such retention means are provided hereinbelow.

Although it is foreseen that in some embodiments modular impellers of the present technology will have only one single impeller vane module, far more often than not impellers having multiple impeller vane modules will be the case. In some such embodiments, there will be an even number (e.g., two) of impeller vane modules, in other such embodiments there will be an odd number (e.g., three) of impeller vane modules.

In some embodiments, each one of the impeller vane modules has a control wire attached thereto and that control wire is manipulable to move that impeller vane module from its unassembled configuration into its assembled configuration. As a skilled addressee would understand, movement of devices having been percutaneously transcatheterly delivered to a site within the body via control wire is known in the art, and thus no further description of the principle need be provided herein.

In some embodiments, the control wires of the impeller vane modules extend through a channel in the impeller hub module. Typically, in such cases, the purpose of the channel is to assist in ensuring the correct positioning of the control wires and/or in preventing the control wires from interfering with or being interfered with by other structures, elements or components (as the case may be). This, however, is not required to be the purpose of such channel in any particular embodiment.

In some embodiments, each control wire of each of the impeller vane modules extends through a discrete channel in the impeller hub module. Such discrete channels may be in place of or in addition to the channel referred to in the previous paragraph. Again, the purpose of such discrete channels may be to assist in ensuring the correct positioning of the control wires and/or in preventing the control wires from interfering with or being interfered with by other structures, elements or components (as the case may be). This, however, is not required to be the purpose of such channels in any particular embodiment.

As a non-limiting example, it is foreseen that in some embodiments, each control wire may extend from its impeller vane module through a discrete channel in the impeller hub module and then to a common channel in the impeller hub module. In some embodiments, the wires may be joined to a single wire (e.g., within the common channel) which then extends proximally through the conduit system (e.g., vasculature) for manipulation by the surgeon (e.g., outside of the body of the patient). In such embodiments, the surgeon need only manipulate that single wire, which causes simultaneous movement of the control wires of each of the impeller vane modules.

As was discussed hereinabove, in the context of the present technology, in different embodiments the impeller vane modules are retained in their assembled configuration via different means. For example, in some embodiments, each one of the impeller vane modules is retained in its assembled configuration solely via tension in its control wire.

In other embodiments, the impeller hub module has a plurality of impeller hub connectors (e.g., connectors associated with the impeller hub module). Each one of the impeller vane modules further has a base (e.g., a structure to which the elements of the impeller vane module are attached (e.g., the portion of the impeller vane)). The base has an impeller vane module connector (e.g., a connector associated with the impeller vane module). The impeller vane module connector and at least one of the impeller hub module connectors are structured to releasably connect to each other. Finally, each one of the impeller vane modules is retained in its assembled configuration via, at least in part, releasable connection of its impeller vane module connector to at least one of the impeller hub module connectors In the context of the present technology, releasable connection of an impeller vane module connector to at least one of the impeller hub module connectors may be achieved in a number of ways. As a non-limiting example, such releasable connection may be achieved by means of a mechanical interlock between the connectors, which, in various embodiments, could be at least by one or more of a sliding interconnection, a screwing interconnection, an expanding interconnection, and/or a frictional interconnection. As another non-limiting example, in various embodiments, such releasable connection may be achieved by a magnetic interlock, the magnetic interlock being in place of or in addition to a mechanical interlock (or other type of connector). Additionally, in some such embodiments, the control wires of the various impeller vane modules are tensioned as well to assist in retaining the impeller vane modules in their assembled configuration.

In some embodiments, the base of each impeller vane module has a proximal end and an impeller vane module secondary connector on the proximal end. The impeller vane module secondary connector is structured and arranged to releasably connect to a corresponding impeller hub module secondary connector on the impeller hub module when the impeller vane module is in its assembled configuration. The releasable connection of these secondary connectors may be achieved by any appropriate means, including those described in the previous paragraph in relation to the "primary" connectors.

In some embodiments, the control wire of each one of the impeller vane modules is detachable from that one of the impeller vane modules when that one of the impeller vane modules is in its assembled configuration. In some such embodiments, detached control wires of impeller vane modules are re-attachable to at least one of the impeller vane modules when that one of the impeller vane modules is in its assembled configuration. E.g., in some embodiments, a detached control wire may be re-attached only to the impeller vane module from which it was detached, and in other embodiments, a detached control wire may be re-attached to any impeller vane module (irrespective of whether that wire had previously been attached to that impeller vane module or not). In embodiments where present, no particular means of attachment, detachment, and/or re-attachment is required. Any such means not incompatible with the delivery, assembly, operation, and removal of the modular impeller, nor incompatible with its use inside a body, is within the scope of the present technology.

In many embodiments, the device further comprises a motor. The motor is operatively connectable to the impeller hub module for rotating the impeller. E.g., the motor generates torque, which is transmitted via the operative connection to the impeller hub, to cause the rotation of the impeller hub.

In some embodiments, the device further comprises a flexible drive shaft operatively connected to the motor and to the impeller hub module, for transmitting torque from the motor to the impeller hub module to rotate the impeller. The use of a flexible drive shaft permits, in some embodiments, the motor to remain outside of the body of the patient even during operation of the device. In such embodiments the flexible drive shaft extends through the vasculature of the patient to the device.

In some embodiments, the device further comprises a hollow control cable having a lumen therein. The control cable may, as a non-limiting example, be used to manipulate the device or a component or components thereof, similarly to the manner in which the control wires (where present) may be used to manipulate the impeller vane modules. (In the context of the present specification no actual difference in the structures covered by a "cable" vs. a "wire" is intended by the use of these two different terms. Two different terms have only been used to make the reading and comprehension of the present specification easier for the reader).

In some embodiments, the flexible drive shaft is rotatably disposed within the lumen of the control cable. In such cases the control cable may protect the conduit system of the body from damage caused by the rotation of the flexible drive shaft. In some embodiments, the flexible drive shaft is itself hollow, having a lumen therein. In other embodiments, multiple discrete lumens are present. The control wires of the impeller vane modules may extend through one of the lumens. In some embodiments each of the control wires may extend through a separate one of the discrete lumens; in others, multiple control wires may extend through a single lumen. In some embodiments, each of the control wires extends to a proximal end of the flexible drive shaft and is secured in place at the proximal end of the flexible drive shaft by a releasable fastener. In some embodiments, at least one lumen of the flexible drive shaft contains a heat transfer fluid. One potential use of such a fluid could be to transfer heat generated by the rotation of the flexible driveshaft (e.g., when the device is in operation) outside of the body of the patient. Other potential uses of such a fluid could be as a continuous or intermittent fluid purge from the outside of the body through the lumen of the control cable and into the vasculature to flush the device (to avoid blood clot deposits), or to lubricate an interface(s) between rotating and non-rotating components of the device.

In some embodiments, the device further comprises a housing in which the motor is disposed. The motor is operatively connectable to the impeller hub module via a drive shaft. And, the housing, the motor, the drive shaft, and the impeller hub module form a single implantable unit. The single implantable unit is dimensioned and shaped to be deliverable to the delivery site within the conduit of the conduit system of the mammalian body via the catheter. The use of such a structure permits, in some embodiments, the motor to be implanted within the patient at the implantation site.

In some such embodiments, the device further comprises a hollow control cable having a lumen therein and having a distal end at least indirectly (i.e., directly or indirectly) attached to the housing. In some such embodiments, the device further comprises electrical wiring in electrical communication with the motor for providing electrical power to the motor, the electrical wiring extending within the lumen of the control cable. In some such embodiments, the control wires of the impeller vane modules extend through the lumen of the control cable (irrespective of whether the electrical wiring extends the lumen of the control cable). In some embodiments, a purge system with purge fluid going through a lumen in the control cable around the motor wires into the motor housing and exiting at the interface between the motor and the impeller hub module may also be present.

In some embodiments, the device further comprises a wire network. The wire network has a proximal end and a distal end. The wire network is connected at its proximal end to a component of the device independent from rotational movement of the impeller hub module (e.g., a component that does not rotate when the impeller hub module (and thus the impeller) rotates). The wire network has a collapsed configuration and an expanded configuration and is overcomably biased towards the expanded configuration. When the wire network is in its collapsed configuration it is dimensioned and shaped to be deliverable to the delivery site within the conduit of the conduit system of the mammalian body via the catheter.

In some such embodiment, when the wire network is in the collapsed configuration it surrounds at least part of the impeller hub module. And, when the wire network is in the expanded configuration, it surrounds at least the vanes of the impeller without interfering with operation of the impeller.

In some such embodiments, the wire network, when in the expanded configuration, is dimensioned and shaped to exert a force on a wall of the conduit into which it is implanted at the implantation site (e.g., of at least one of the conduit and another conduit of the conduit system of the mammalian body). And the force is sufficient to anchor the device in place at the implantation site.

In some embodiments, the distal end of the wire network forms a variable-size distal opening. When the wire network is in the collapsed configuration: (i) That opening is of an insufficient size to permit impeller vane modules to pass through that opening. (ii) Each one of the impeller vane modules is in its unassembled configuration distal to the impeller hub module. (iii) The control wires of the impeller vane modules extend through that opening. When the wire network is in the expanded configuration, that opening is of a sufficient size to permit impeller vane modules to pass through that opening, and each of the impeller vane modules is moveable through that opening towards its assembled configuration.

In some embodiments, the impeller hub module has a distal spindle. The device further includes a distal bearing hub distal to the impeller hub module. The distal bearing hub has a bearing supporting the distal spindle of the impeller hub module. The work network has distal wires extending distally beyond a distal end of the impeller hub module. The distal wires are connected to the distal bearing hub. When the wire network is in its expanded configuration: (i) The wire network has a plurality of distal gaps bounded at least in part by at least one of the distal wires. The control wire of each one of the impeller vane modules passes through a one of the gaps. That one of the gaps is of a sufficient size to permit that one of the impeller vane modules to pass through that one of the gaps. That one of the impeller modules is movable through that one of the gaps towards its assembled configuration.

Notwithstanding the fact that the present technology was developed as an alternative to expandable impeller vanes as was described hereinabove, there is nothing about the present technology per se that would prevent the vanes of impellers of the present technology from being expandable (between a collapsed configuration and an expanded configuration), assuming the design of the device otherwise permits such expandability.

Notwithstanding the fact that hereinabove the impeller vane modules have been described as unitary structures, it is foreseen that the impeller vane modules could themselves be of a modular design. Thus, for example, embodiments are foreseen wherein each of the impeller vane modules has at least two separate impeller vane module components, and that each impeller vane module is formed in vivo when all of the impeller vane module components of which it is made are assembled together. This may be achieved, for example, by using control wires and connectors as described hereinabove.

In some embodiments: The impeller is an axial impeller. A diameter of the impeller is between 4 mm and 35 mm inclusive. An operating speed of the impeller is between 1000 RPM and 60,000 RPM inclusive. An output of the impeller is between 0.5 liters/min. and 10 liters/min. inclusive.

In some embodiments: The mammalian body is a human body. The conduit system of the human body is a vascular system of the human body. The conduit of the vascular system is one of an aorta, a left ventricle, a vena cava, a pulmonary artery, and a right ventricle.

In some embodiments, the catheter is a delivery sheath. In some embodiments, the device further comprises a loader connectable at least indirectly (i.e., directly or indirectly) to the delivery sheath for loading the device into the delivery sheath. At least the impeller hub module and the impeller vane modules in their unassembled configuration are within the loader in series one distal to another, with the impeller hub module being proximal to the impeller vane modules.

In another aspect, implementations of the present technology provide a method of implanting a mammalian body implantable fluid flow influencing device as described hereinabove into conduit of a conduit system of a mammalian body, the method comprising:
a) obtaining access to the conduit system of the mammalian body;
b) guiding a delivery sheath to the delivery site;
c) inserting the impeller vane modules in their unassembled configuration distal end first into the delivery sheath in series one after another;
d) inserting the impeller hub module into the delivery sheath;
e) guiding the impeller vane modules and the impeller hub module within the delivery sheath to the delivery site;
f) promoting exit of the impeller vane modules from the delivery sheath at the delivery site;
g) promoting exit of the impeller hub module from the delivery sheath at the delivery site;
h) withdrawing the delivery sheath from the body; and
i) manipulating the control wires of the impeller vane modules to move the impeller vane modules into their assembled configuration.

General

In the context of the present specification, the words "first", "second", "third", etc. have been used as adjectives only for the purpose of allowing for distinction between the nouns that they modify from one another, and not for the purpose of describing any particular relationship between those nouns. Thus, for example, it should be understood that the use of the terms "first unit" and "third unit" is not intended to imply any particular type, hierarchy or ranking (for example) of/between the units. Nor is their use (by itself) intended imply that any "second unit" must necessarily exist in any given situation.

In the context of the present specification, the word "embodiment(s)" is generally used when referring to physical realizations of the present technology and the word "implementations" is generally used when referring to methods that are encompassed within the present technology (which generally involve also physical realizations of the present technology). The use of these different terms is not intended to be limiting of or definitive of the scope of the present technology. These different terms have simply been used to allow the reader to better situate themselves when reading the present lengthy specification.

Embodiments and implementations of the present technology each have at least one of the above-mentioned objects and/or aspects, but do not necessarily have all of them. It should be understood that some aspects of the present technology that have resulted from attempting to attain the above-mentioned object may not satisfy this object and/or may satisfy other objects not specifically recited herein.

Additional and/or alternative features, aspects and advantages of embodiments and/or implementations of the present technology will become apparent from the following description, the accompanying drawings and the appended claims.

BRIEF DESCRIPTION OF THE DRAWINGS

For a better understanding of the present technology, as well as other aspects and further features thereof, reference is made to the following description, which is to be used in conjunction with the accompanying drawings, where.

DETAILED DESCRIPTION OF SOME EMBODIMENTS AND IMPLEMENTATIONS

Introduction

Figure 1A:
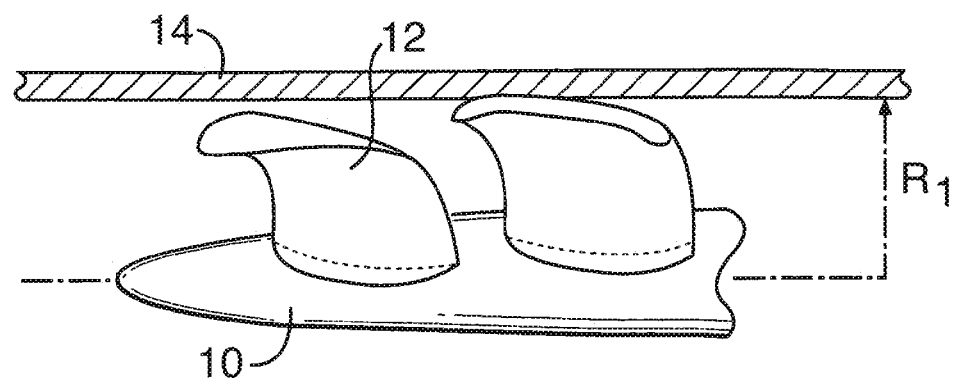
FIG. 1A is a prior art expandable impeller as shown in FIG. 1A of McBride et al. and described therein.
Figure 1B:
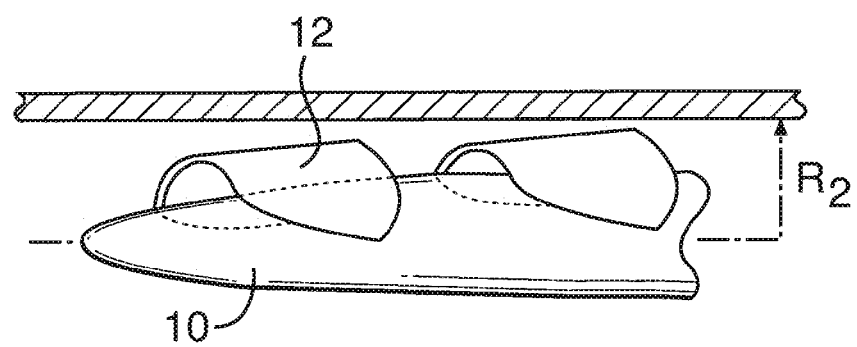
FIG. 1B is a prior art expandable impeller as shown in FIG. 1B of McBride et al. and described therein.
Figure 2:
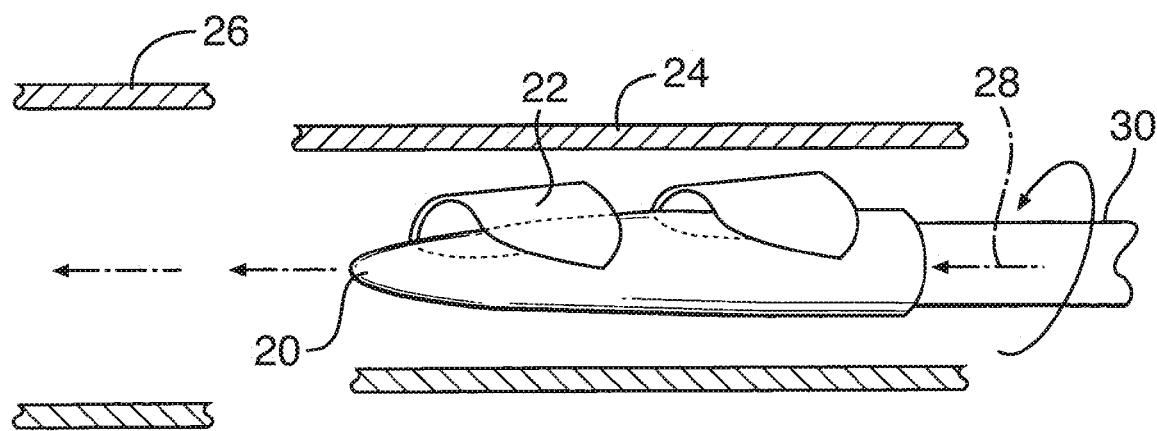
FIG. 2 is a prior art expandable impeller as shown in FIG. 2 of McBride et al. and described therein.
Figure 3:
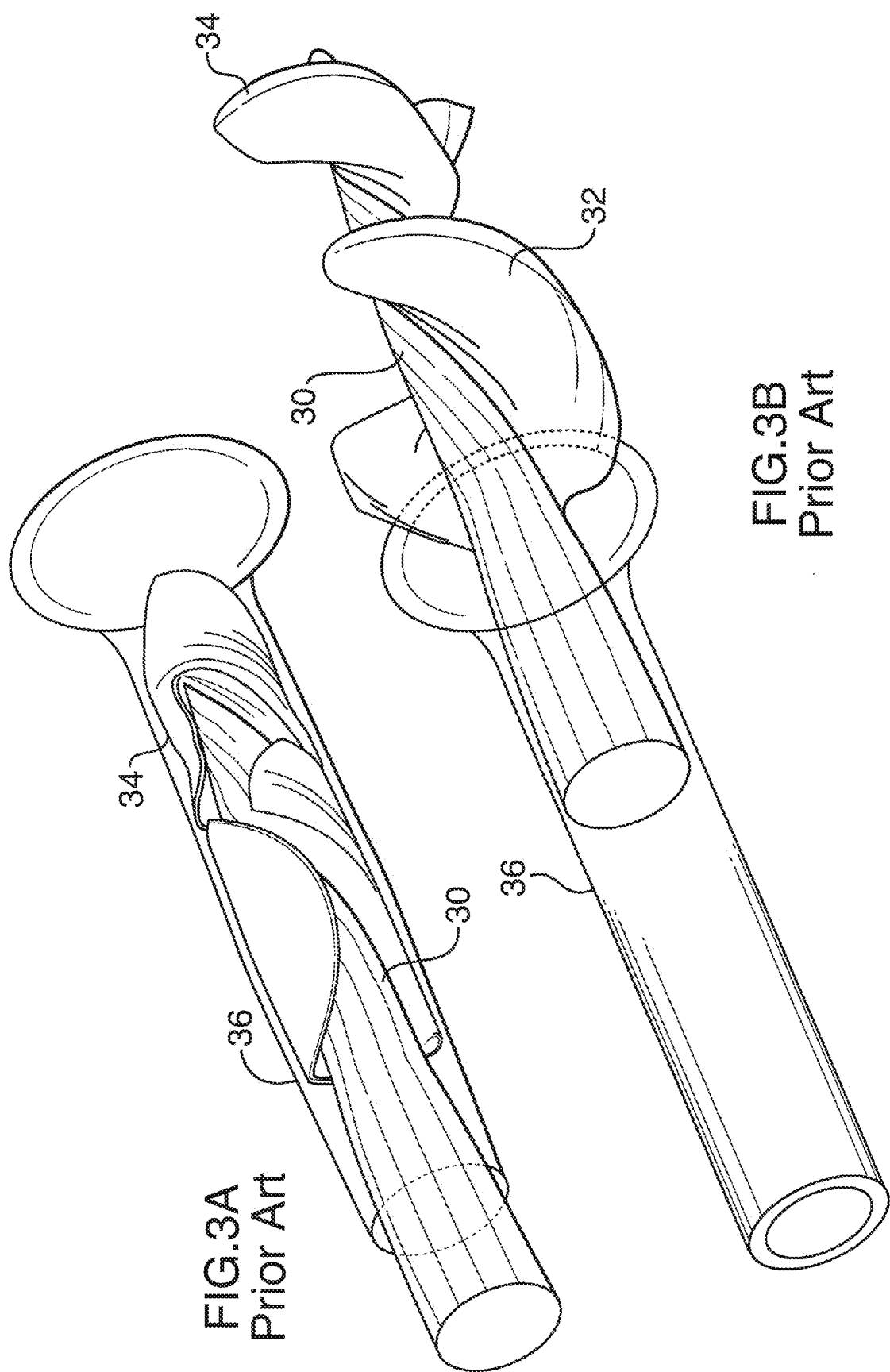
FIG. 3A is a prior art expandable impeller as shown in FIG. 3A of McBride et al. and described therein.
FIG. 3B is prior art expandable impeller as shown in FIG. 3B of McBride et al. and described therein.
Figure 4:
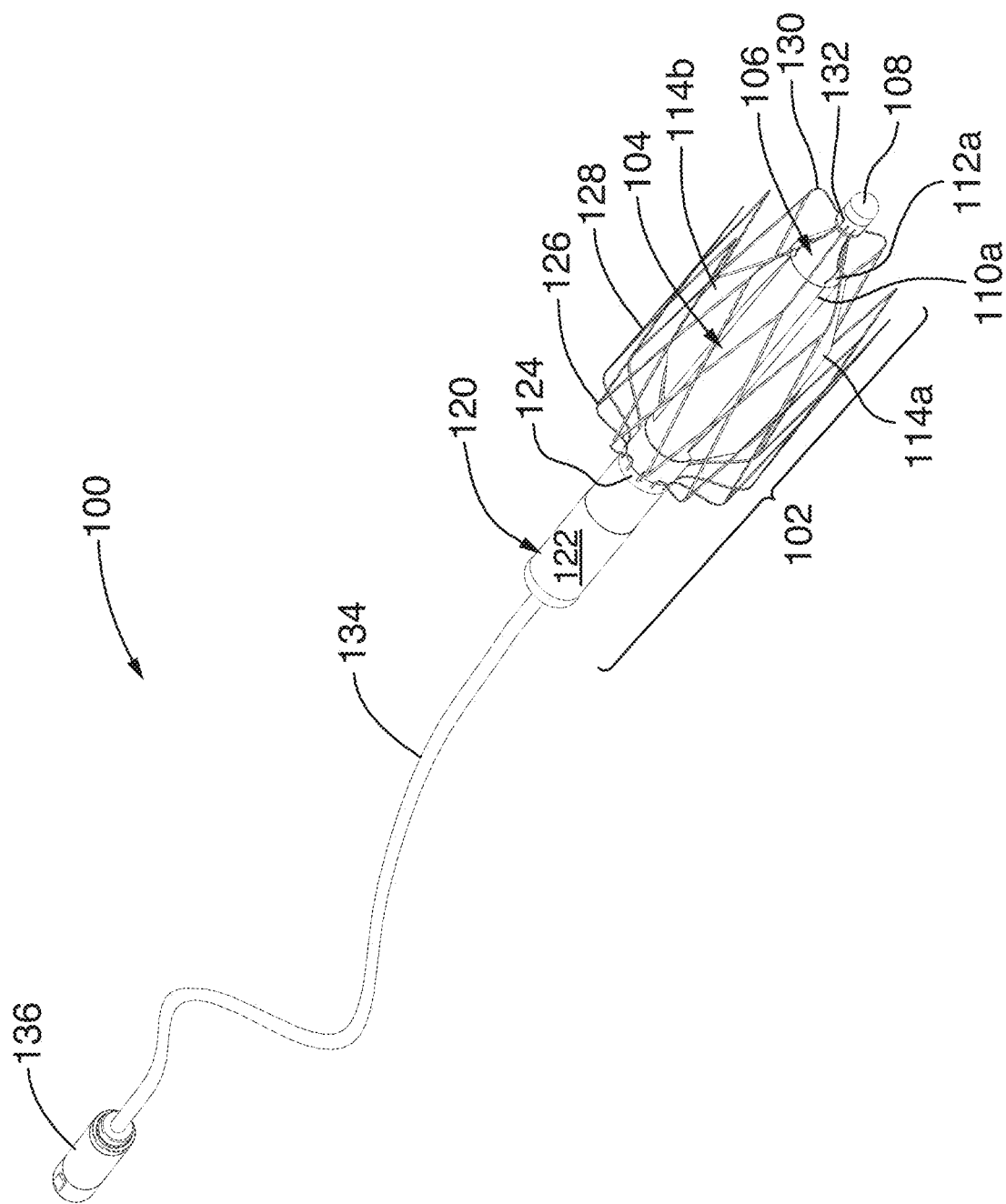
FIG. 4 is an isometric view of a percutaneously transcatheterly implantable intravascular blood pump being a first embodiment of the present invention, taken from the distal end thereof.
Figure 5:
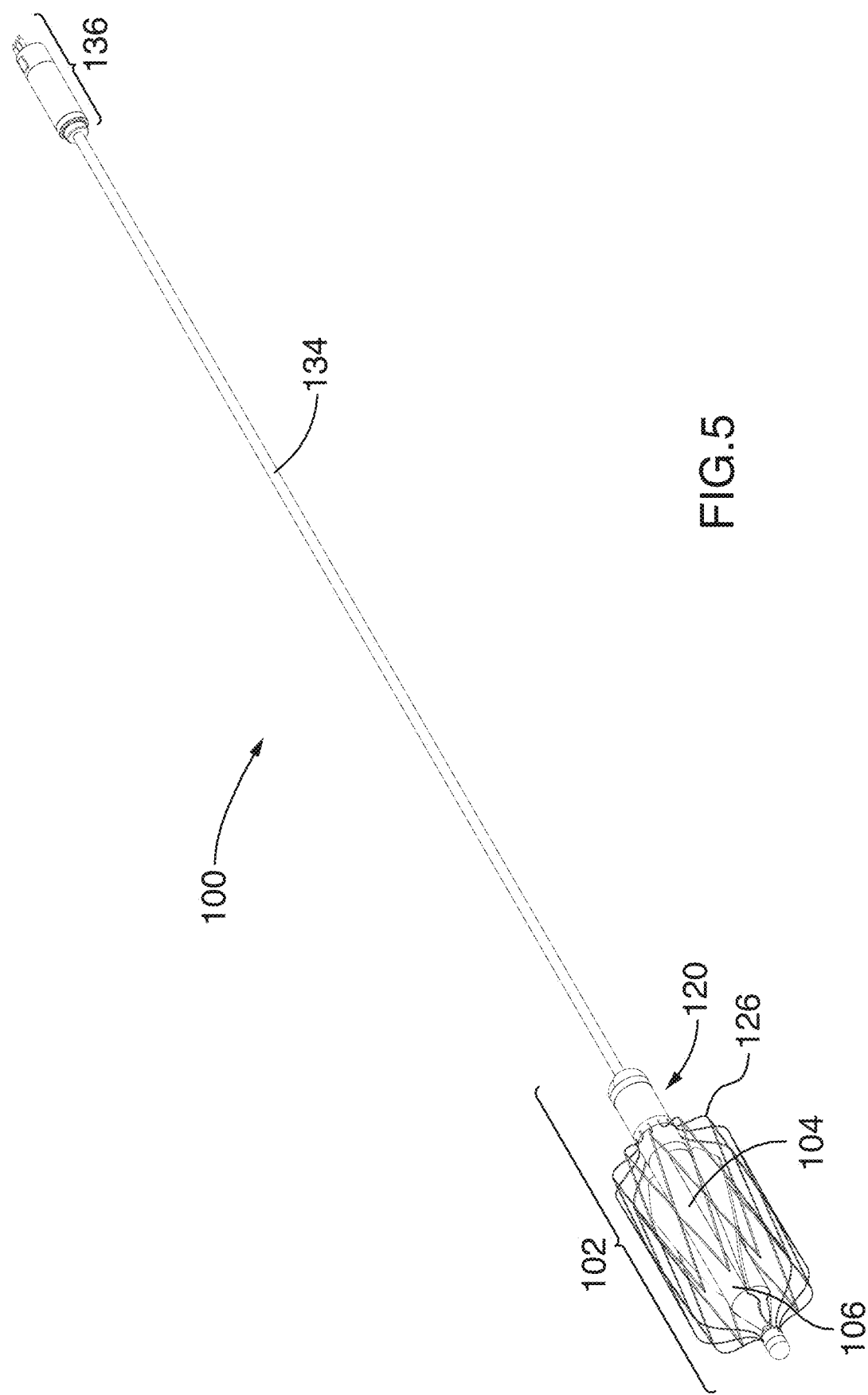
FIG. 5 is another isometric of the blood pump of FIG. 4.

Referring to FIGS. 4 and 5, there is shown a mammalian body implantable fluid flow influencing device 100, which is one embodiment of the present technology. It is to be expressly understood that the device 100 is merely one embodiment, amongst many, of the present technology. Other embodiments are also described hereinbelow. Thus, the description thereof that follows is intended to be only a description of illustrative examples of the present technology. This description is not intended to define the scope or set forth the bounds of the present technology. In some cases, what are believed to be helpful examples of modifications to the device 100 and/or other embodiments may also be set forth hereinbelow. This is done merely as an aid to understanding, and, again, not to define the scope or set forth the bounds of the present technology. These modifications are not an exhaustive list, and, as a skilled addressee would understand, other modifications are likely possible. Further, where this has not been done (i.e., where no examples of modifications have been set forth), it should not be interpreted that no modifications are possible and/or that what is described is the sole manner of implementing that element or feature of the present technology. As a skilled addressee would understand, this is likely not the case. In addition, it is to be understood that the device 100 may provide in certain instances a simple embodiment of the present technology, and that where such is the case it has been presented in this manner as an aid to understanding. As a skilled addressee would understand, various embodiments of the present technology are of a greater complexity.

Additional Information & Incorporations-by-Reference

Device 100 is a percutaneously transcatheterly implantable intravascular blood pump, which may be used as a ventricular assist device (a "VAD"). As a skilled addressee would understand, percutaneously transcatheterly implantable intravascular blood pumps are well known in the art. Thus, for purposes of brevity, no has been made to describe herein details of the device 100 (or other embodiments of the present technology) with which the skilled addressee would be familiar. However, to facilitate understanding of such devices (e.g., by readers not skilled in the art), reference may be had to one or more of the following patent documents, which are incorporated herein by reference in their entirety for all purposes:

U.S. Pat. No. 4,625,712 (Wampler), issued Dec. 2, 1986, entitled "High-Capacity Intravascular Blood Pump Utilizing Percutaneous Access";

U.S. Pat. No. 7,022,100 B1 (Aboul-Hosn et al.), issued Apr. 4, 2006, entitled "Guidable Intravascular Blood Pump and Related Methods";

U.S. Pat. No. 7,070,555 B2 (Siess), issued Jul. 4, 2006, entitled "Intracardiac Blood Pump";

U.S. Pat. No. 7,393,181 B2 (McBride et al.), issued Jul. 1, 2008, entitled "Expandable Impeller Pump";

U.S. Pat. No. 7,841,976 B2 (McBride et al.), issued Nov. 30, 2010, entitled "Heart Assist Device with Expandable Impeller Pump";

U.S. Pat. No. 7,998,954 B2 (Bollin), issued Aug. 16, 2011, entitled "Implantable Heart Assist System and Method of Applying Same";

U.S. Pat. No. 9,421,311 B2 (Tanner et al.), issued Aug. 23, 2016, entitled "Motor Assembly for Catheter Pump";

U.S. Pat. No. 9,446,179 B2 (Keenan et al.), issued Sep. 20, 2016, entitled "Distal Bearing Support";

U.S. Pat. No. 9,872,947 B2 (Keenan et al.), issued Jan. 23, 2018, entitled "Sheath System for Catheter Pump";

U.S. Pat. No. 10,478,538 B2 (Scheckel et al.), issued Nov. 19, 2019, entitled "Flexible Catheter with a Drive Shaft";

U.S. Pat. App. Pub. No. 2010/0268017 A1 (Siess), published Oct. 21, 2010, entitled "Intracardiac Pumping Device";

U.S. Pat. App. Pub. No. 2011/0004046 A1 (Campbell et al.), published Jan. 6, 2011, entitled "Blood Pump with Expandable Cannula";

U.S. Pat. App. Pub. No. 2012/0101455 A1 (Liebing), published Apr. 26, 2012, entitled "Shaft Arrangement Having a Shaft Which Extends within a Fluid-Filled Casing";

U.S. Pat. App. Pub. No. 2012/0172655 A1 (Campbell et al.), published Jul. 5, 2012, entitled "Impeller Housing for Percutaneous Heart Pump";

U.S. Pat. App. Pub. No. 2012/0178985 A1 (Walters et al.), published Jul. 12, 2012, entitled "Percutaneous Heart Pump";

U.S. Pat. App. Pub. No. 2012/0178986 (Campbell et al.), published Jul. 12, 2012, entitled "Percutaneous Heart Pump";

U.S. Pat. App. Pub. No. 2016/0256620 A1 (Scheckel et al.), published Sep. 8, 2016, entitled "Flexible Catheter with a Drive Shaft"; and U.S. Pat. App. Pub. No. 2020/0330665 A1 (Josephy et al.), published Oct. 22, 2020, entitled "Cooled Mechanical Circulatory Support System and Method of Operation".

The above list is not intended to be a complete list for any purpose. It is only intended to provide some examples of some documents believed to be useful. Percutaneously transcatheterly implantable intravascular blood pumps have been described in the literature at least since the 1980's, and thus there are many documents that might be helpful that are not set forth above.

In addition, the following patent documents commonly owned by the assignee of the present application are also incorporated herein by reference in their entirety for all purposes. These documents may also provide additional background, especially to the unskilled reader:

Int'l. Pat. App. Pub. No. WO 2020/198765 A2 (Puzzle Medical Devices Inc.), published Oct. 1, 2020, entitled "Modular Mammalian Body Implantable Fluid Flow Influencing Device and Related Methods"; and Int'l Pat. App. No. PCT/US2021/012083 (Puzzle Medical Devices Inc, et al.), filed Jan. 4, 2021, entitled "Mammalian Body Conduit Intralumenal Device and Lumen Wall Anchor Assembly, Components Thereof and Methods of Implantation and Explantation Thereof".

General

At a high level, device 100, has the following major components: an axial impeller 104, a drive unit 120, and an anchor 126. Device 100 also has a control cable 134 extending proximally from the proximal end of the drive unit 120, and a proximal end unit 136 at the proximal end of the control cable 134. Each of the foregoing components is discussed in further detail hereinbelow.

The device 100 being a percutaneously transcatheterly implantable intravascular blood pump, in use, when appropriately implanted within the vasculature of a patient, is operable to increase the patient's native blood flow rate. Typically, the device is employed as a VAD or a cardiac assist device in cases where the patient's heart is unable to pump a sufficient amount of blood on its own to provide enough blood flow to their peripheral organs (in the case of the left heart) or to their lungs (in the case of the right heart).

Impeller

Figure 18:
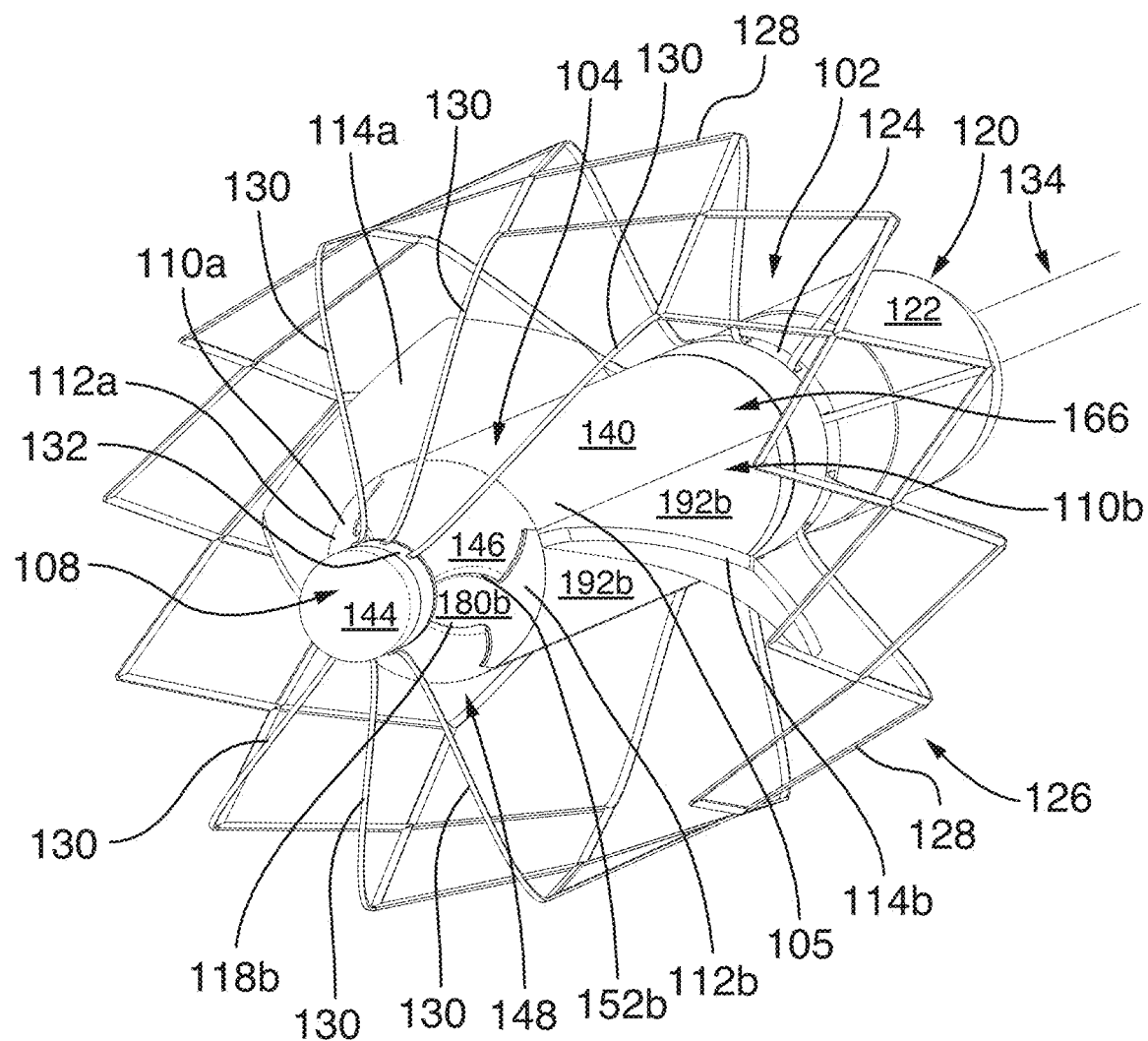
FIG. 18 is another isometric view of the blood pump of FIG. 4, taken from the distal end thereof, with both the first impeller vane module and the second impeller vane module being their assembled configurations such that the impeller is fully assembled.
Figure 19:
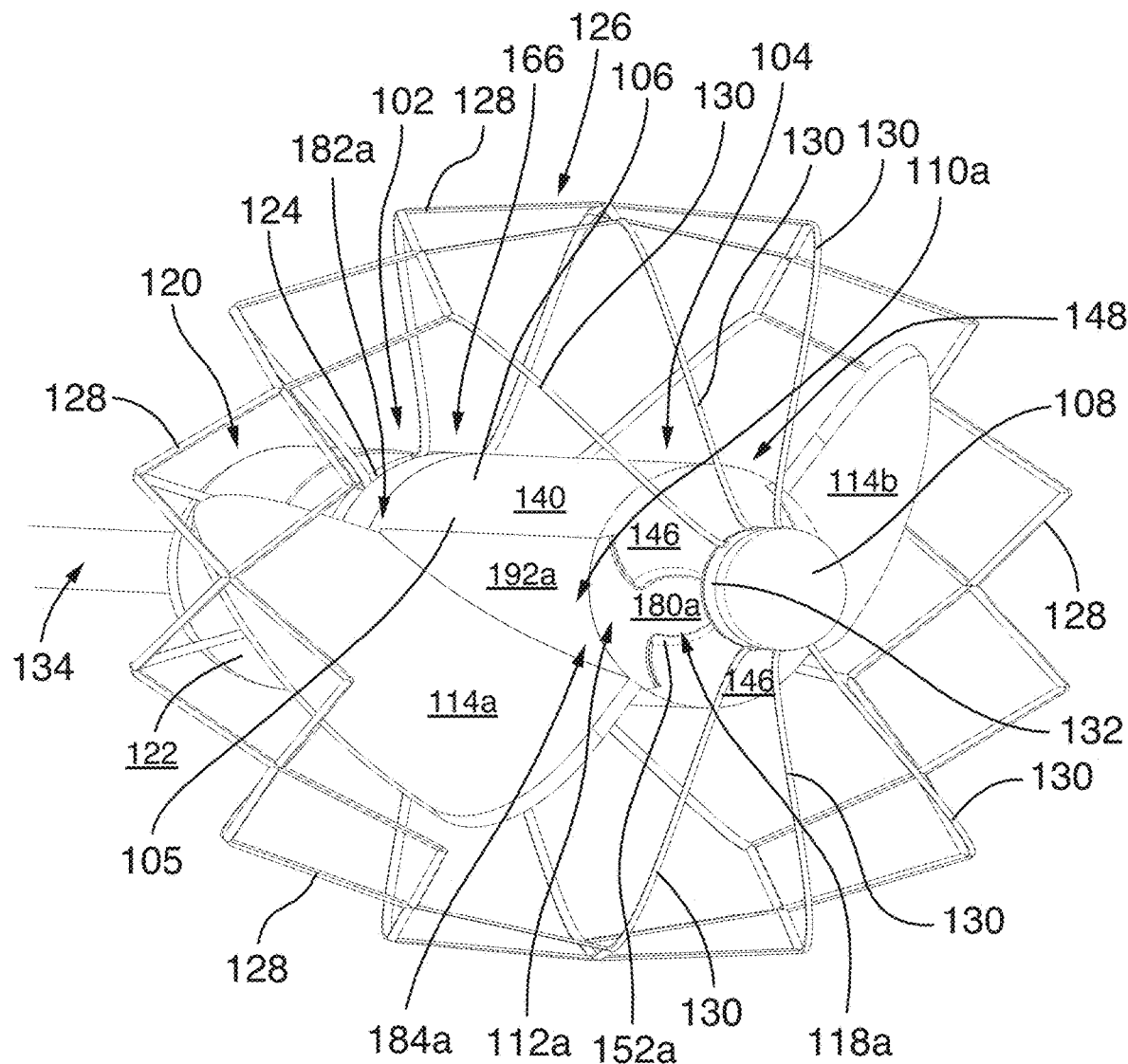
FIG. 19 is still another isometric view of the blood pump of FIG. 4, taken from the distal end thereof, with both the first impeller vane module and the second impeller vane module being their assembled configurations such that the impeller is fully assembled.

Referring to FIGS. 18 and 19 in particular, the impeller 104 of the device 100 has a central hub 105 and two vanes 114a, 114b projecting outward from the hub 105. The impeller 104 is considered axial impeller, in view of its overall dimensions and as the fluid being pumped by the impeller is pushed by the vanes generally in a direction parallel to the longitudinal axis of the impeller 104 (e.g., an axis colinear with the longitudinal axis 138 of the device 100—hereinafter, for ease of understanding, the longitudinal axes of the impeller 104, the device 100, the impeller hub module 106, and the impeller hub 105 are all colinear in this embodiments and are all thus labeled as 138).

As would be understood by the skilled addressee, in most embodiments, the entirety of the flow fluid generated by axial impellers is not axial, there is some radial component. The presence of such radial component is generally tolerable and does not mean that the impeller in question is not an axial impeller.

Impeller 104 is a modular impeller. Thus, impeller 104 is made of different modules that are separate structures from one another, but that are combinable together (e.g., assemblable) in vivo to make a complete, fully operational impeller 104. In FIGS. 18 and 19, the assembled fully-operational impeller 104 is shown. In this embodiment, the impeller 104 has three separate modules, one impeller hub module 106 and two impeller vane modules (i.e., a first impeller vane module 110a and a second impeller vane module 110b).

Figure 6:
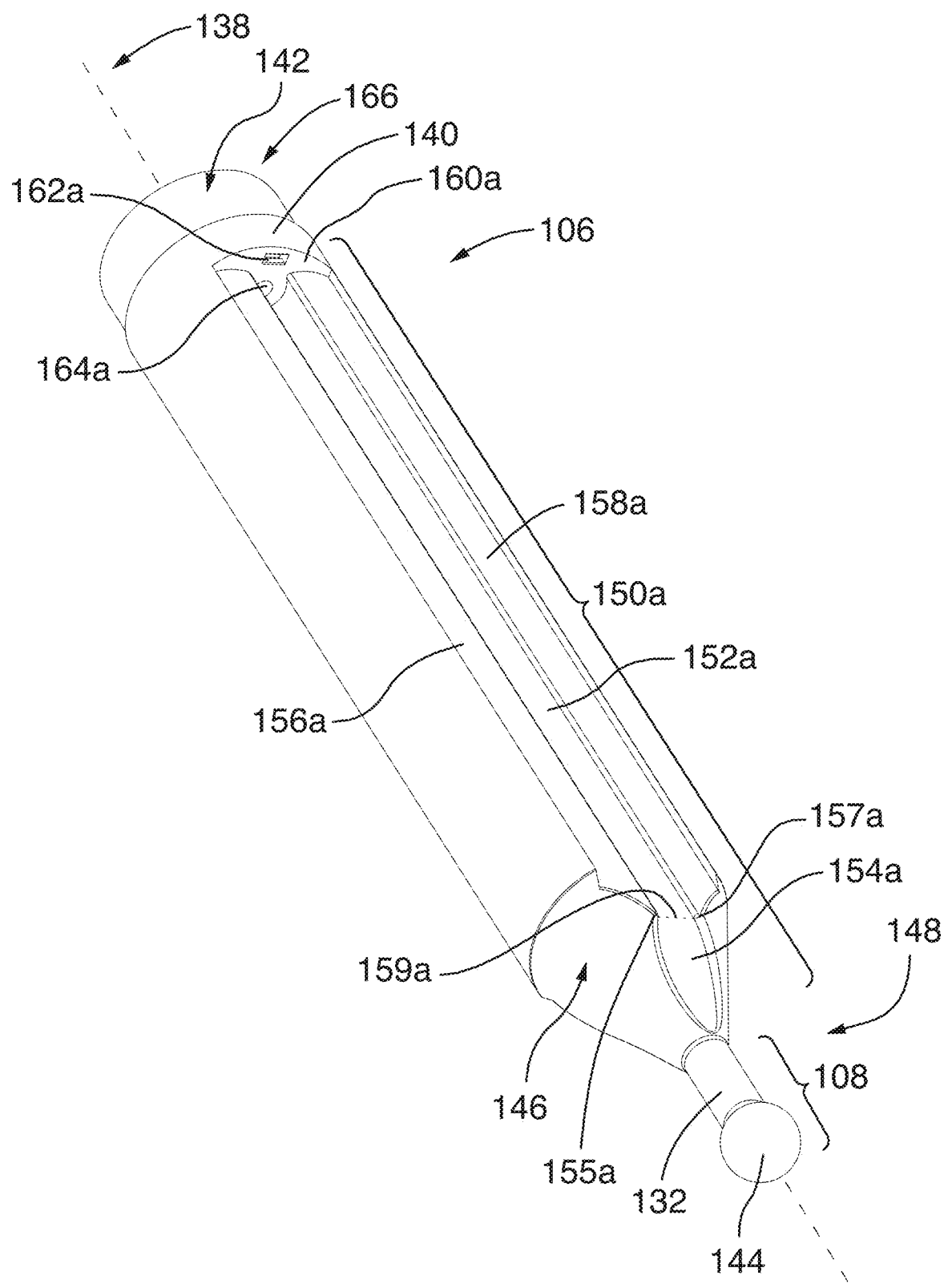
FIG. 6 is an isometric view of the impeller hub module of the blood pump of FIG. 4, taken from the distal end thereof.

The impeller hub module 106 is shown by itself in FIG. 6. As can be seen in FIG. 6, the impeller hub module 106 is elongate body generally having the form of a right circular cylinder. Thus, a cross-section of the impeller hub module 106 taken in a plane perpendicular to the longitudinal axis 138 would be a circle were it not for the present of the impeller hub module connectors 150a, 150b (described hereinbelow); and, this is the case for cross-sections taken anywhere along the longitudinal axis 138 (in this embodiment).

The impeller hub module has a distal end 148 and a proximal end 166. In the context of the present specification, the terms "distal" and "proximal" are defined with respect to the location at which the surgeon is accessing the vasculature of the of the patient into which the device is being implanted. Thus, "distal" is further from the surgeon, and "proximal" is closer to the surgeon. The distal end of a component enters the body of the patient before the proximal end in this embodiment.

The impeller hub module 106 has two impeller hub module connectors, a first impeller hub module connector 150a associated with the first impeller vane module 110a and a second impeller hub connector 150b associated with the second impeller vane module 110b. In this embodiment, the first impeller hub module connector 150a and the second impeller hub module connector 150b are identical. (This is not the case in all embodiments, as in some embodiments each of the impeller hub module connectors are not identical.)

As can be well seen in FIG. 6, each impeller hub module connector 150a, 150b is accessible and viewable from the exterior of the impeller hub module 106. Each impeller hub module connector 150a, 150b has a channel 152a, 152b that extends parallel to the longitudinal axis 138 of the device 100 (and the longitudinal axis 138 of the impeller hub module 106 itself). In this embodiment, each channel 152, 152b, is generally circular in cross section (albeit with a small arc missing), as can be seen in FIG. 6. The ends 155a, 157a of the missing arc the plane perpendicular to the longitudinal axis 138, when joined together by a line 159a, form a segment of the circle in that plane that has a length that is less than the diameter of that circle.

Each channel 152a, 152b has a proximal end (not labelled) at the proximal end 166 of the impeller hub module 106 and a distal end (not labelled) at the distal end 148 of the impeller hub module 106. Each proximal end is a "wall" (e.g., a generally planar surface) 160a, 160b that is perpendicular to the longitudinal axis 138. In each wall are located a passage 164a, 164b (through a control wire 116a, 116b (respectively) will pass—as is described in further detail below) and the cavity 162a, 162b of a secondary connector 189a, 189b which will also be described hereinbelow. The distal end of each channel 152a, 152b is an opening 154a, 154b. As the distal end 148 of the impeller hub module 106 has a tapered portion 146 (e.g., see FIG. 6), the distal opening 154a, 154b of each channel 152a, 152b are sloped as they extend through the tapered portion 146. Each channel 152a, 152b, thus forms a socket of a dovetail joint, as is further described hereinbelow. Finally, extending on each side of each channel 152a, 152b, is a longitudinally extending shelf 156a, 158a (on the sides of channel 152a), 156b, 158b (on the sides of channel 152b).

In this embodiment, the impeller hub module 106 is made of titanium. In other embodiments, the impeller hub module 106 is made of any other suitable medical grade material (or combination of materials) including composites, metals, alloys or plastics (e.g., PEEK). The impeller hub module 106 is manufactured using conventional techniques appropriate to the material(s) of which it is made.

Figure 7:
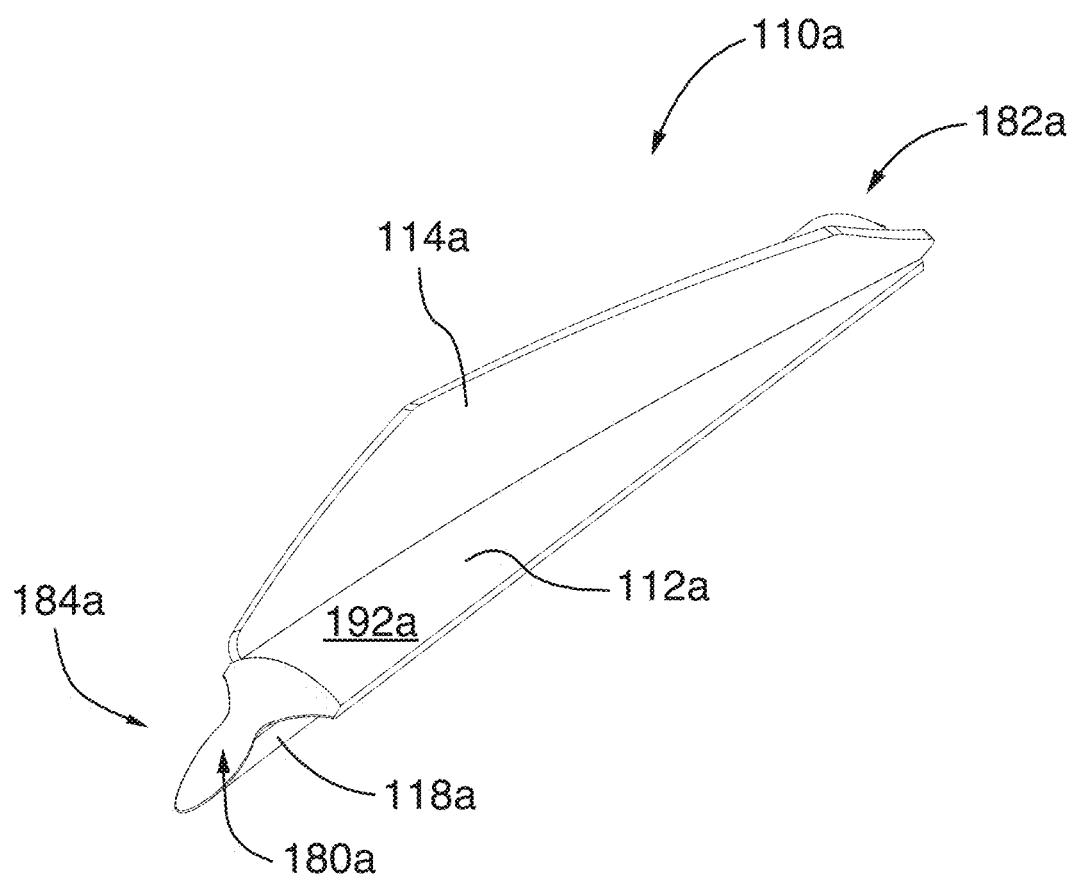
FIG. 7 is an isometric view of a first impeller vane module of the blood pump of FIG. 4, taken from the distal end thereof.
Figure 8:
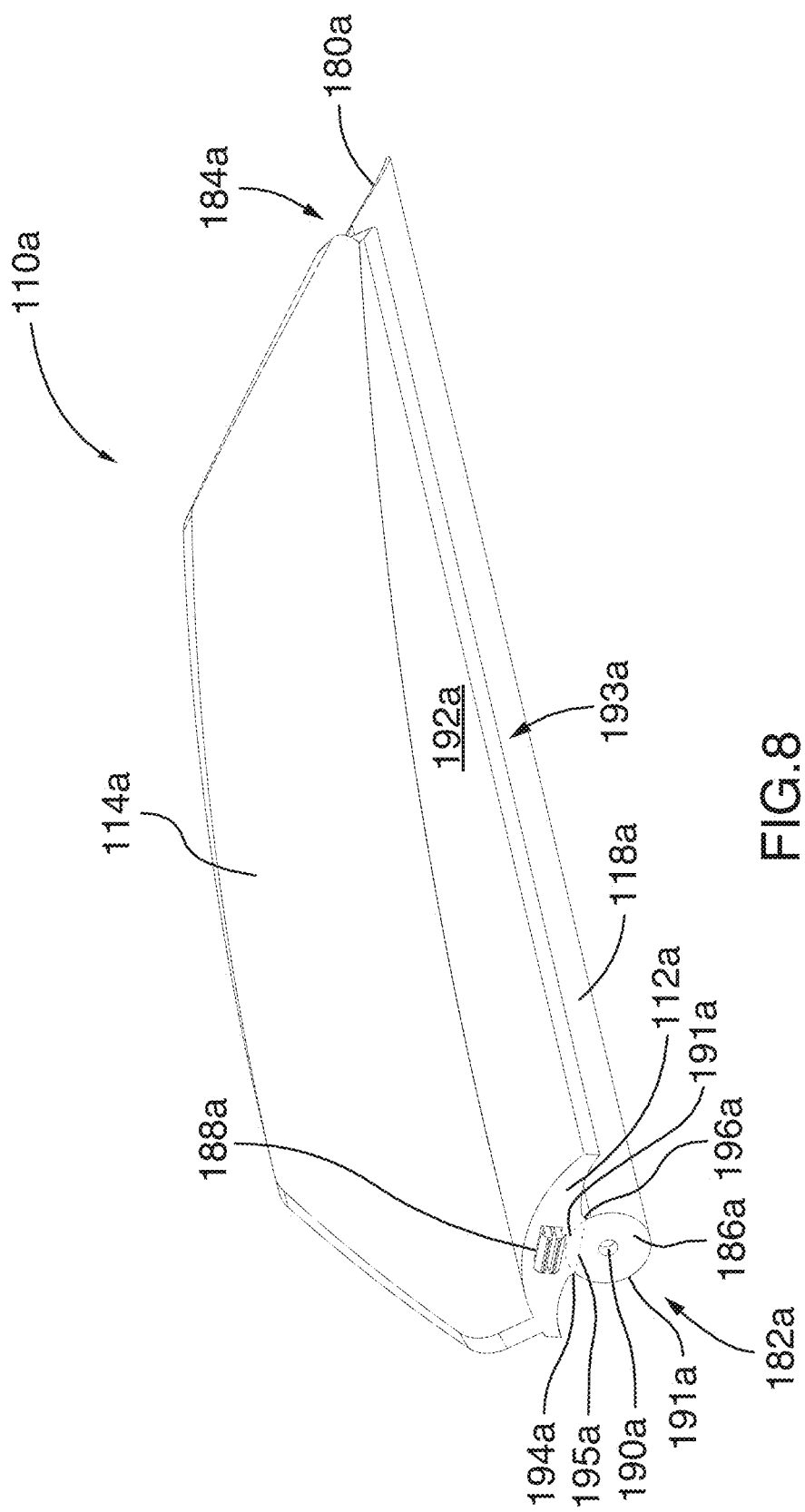
FIG. 8 is an isometric view of the first impeller vane module of FIG. 7, taken from the proximal end thereof.

Referring now to FIGS. 7 and 8, the first impeller vane module 110a is shown. (In this embodiment, the second impeller vane module 110b is identical to the first impeller vane module 110a and thus, will not be specifically described herein. (In other embodiments this is not the case.)) The first impeller vane module 110a is an elongate structure having a proximal end 182a and a distal end 184a. The first impeller vane module 110a has a base 112a, an impeller vane 114a projecting from the base 112a and a first impeller vane module connector 118a extending from the side of the base 112a opposite to that one from which the impeller vane 114a projects. Each of the base 112a, the impeller vane 114a, and the first impeller vane module connector 118a extends the entire length of the impeller vane module 110a from the proximal end 182a to the distal end 184a in this embodiment.

Referring to FIG. 8, in this embodiment, the first impeller vane module connector 118a is generally a right circular cylinder portion 193a of which is connected to the base 112a of the first impeller vane module 110a. A segment 195a of a cross-section of the circle 191a formed by the proximal end 182a wall 186a in a plane perpendicular the longitudinal axis 138 is formed by the line jointing the intersections (194a, 196a) of the circle 191a with the connecting portion 193a. At the center of the circle 191a is a passage 190a leading inside the connector 118a. As will be discussed further below, the passage 190a is for the control wire 116a. Also, projecting proximally from the proximal end 182a wall 186a are detents 188a that form the part of a secondary connector 189a that is disposed on the first impeller vane module 110a. Finally, the distal end 184a has a sloped face 180a (with respect to the longitudinal axis 138)

In this embodiment, the base 112a and the first impeller vane module connector 118a are dimensioned and shaped to complete the part of the hub 105 of the impeller hub module 106 that is "missing" because of the presence of the impeller hub module connector 150a. Thus, the length of the first impeller vane module 110a is the same as the length of the first impeller hub module connector 150a. The first impeller vane module connector 118a has a diameter just slightly smaller than the diameter of the channel 152a, and the length of the segment 159a is just slightly smaller than the length of the segment 195a. The base 112a has a shape that conforms to both the shelves 156a, 158a and to the outer surface 140 of the impeller hub module 106.

In this embodiment, the impeller vane modules 110a, 110b are each made of titanium. In other embodiments, the impeller vane modules 110a, 110b are made of any other suitable medical grade material (or combination of materials) including composites, metals, alloys or plastics (e.g., PEEK). The impeller vane modules 110a, 110b are manufactured using conventional techniques appropriate to the material(s) of which they are made.

Units of the device 100 to be implanted within the patient's body (e.g., the impeller vane modules 110a, 110b, the single implantable unit 102 (the impeller hub module 106 and the motor housing 120)) are dimensioned and shaped to be deliverable through the vasculature of the patient's body via a catheter (e.g., a delivery sheath 198). Depending on the particular patient and the particular delivery site, the maximum size of the catheter that may be used in a particular transcatheter procedure varies. Thus, the surgeon has to select a catheter sized such that the catheter will pass through the minimum available cross-section of the blood vessels of the patient along the path to the delivery site. So, for example, if it were determined that a 12 Fr (4 mm) catheter was to be used in a particular procedure, any units of the device 100 to be delivered through that catheter must be designed such that their dimensions and shapes permit them to be delivered through a catheter of 12 Fr. Thus, the diameter of the minimum-bounding right circular cylinder of each one of those units can be no greater than 4 mm (its radius no greater than 2 mm). In this embodiment, the diameter of the minimum-bounding right circular cylinder of each one of the impeller vane modules 110a, 110b, the impeller hub module 106, and the motor housing 120 (combined to make the single implantable unit 102) is slightly less than 4 mm, so they would be able to be used in the above exemplary procedure. Thus, the diameter of the impeller 104, once assembled, will be larger than 4 mm, without being expendable.

To connect the first impeller vane module 110a to the impeller hub module 106, the proximal end 182a of the first impeller vane module connector 118a of the first impeller vane module 110a is slidden into the channel 152a of the first impeller hub module connector 150a via the distal opening 154a at the distal end 148 of the impeller hub module 106. When the first impeller vane module connector 118a is fully slidden into the channel 152a of the first impeller hub module connector 150a, the proximal end wall 186a at the proximal end of the first impeller vane module 110a registers completely with the proximal end wall 160a of the proximal end of the channel 152a. The first impeller vane module connector 118a acts as the tail in the sliding dovetail connection (with, as was described above, the channel 152a of the first impeller hub connector module 106 acting as the socket). This arrangement results because the outer diameter of the right circular cylinder of the first impeller vane module connector 118a is greater than the length of the segment 159a. Thus, during normal operation of the device, when the impeller 104 is rotating, the first impeller vane module 110a can neither be pulled nor pushed away from its assembled configuration in a direction perpendicular to (or having a component that is perpendicular to) the longitudinal axial 134 of the impeller hub module 106.

Again, when the first impeller vane connection module 118a is fully slidden into the channel 152a until its assembled configuration, the detents 188a of the secondary connector 189a on the first impeller vane module 118a are inserted into and releasably secured within the cavity 162a of the second connector 189a on the end wall 162a of the first impeller hub module connector 150a. Thus, during normal operation of the device, when the impeller 104 is rotating, the first impeller vane module 110a cannot be slidden out of its assembled configuration either.

Again, when the first impeller vane module connector 118a is fully slidden into the channel 152a into its assembled configuration, a portion 192a of the outer surface of the base 112a of the first impeller vane module is shaped to align with and complete the outer surface 140 of the impeller hub module 106, such that the impeller hub 105 (but for the vanes) has the shape of a right circular cylinder. And, the sloped face 180a of the distal end 184a of the first impeller vane module 110a aligns with and completes the tapered portion 146 of the distal end 148 of the impeller hub module 106.

Each of the impeller vane modules 110a, 110b has a center of mass (not shown). The impeller hub module 106 also has a center of mass (not shown), which is located along the longitudinal axis 138 of the impeller hub module 106. The impeller vane modules 110a, 110b are designed (e.g., size, shape, materials of construction, vane design, etc.) such that when the first impeller vane module connector 118a is fully slidden into the channel 152a into its assembled configuration and when the second impeller vane module 118b is fully slidden into the channel 152b into its assembled configuration (e.g., in FIGS. 18 and 19), the center of mass (not shown) of the assembled impeller 104 is located same location as (i.e., is coincident with) the center of mass of the impeller hub module 106. Thus, in this embodiment, the centers of mass of the impeller vane modules 110a, 110b are all equally angularly spaced (i.e., at 180° degrees from one another) around the axis of rotation (i.e., the longitudinal axis 138) of the impeller 104 in a plane perpendicular to the axis 138 containing the center of mass of the impeller hub module 106. And, the centers of mass of the impeller vane modules 110a, 110b are equally radially distant from the axis 138 of the impeller hub module 106 in that plane. In this manner the impeller 104 will be mass balanced, which is optimal for its rotation.

Drive Unit

Figure 21:
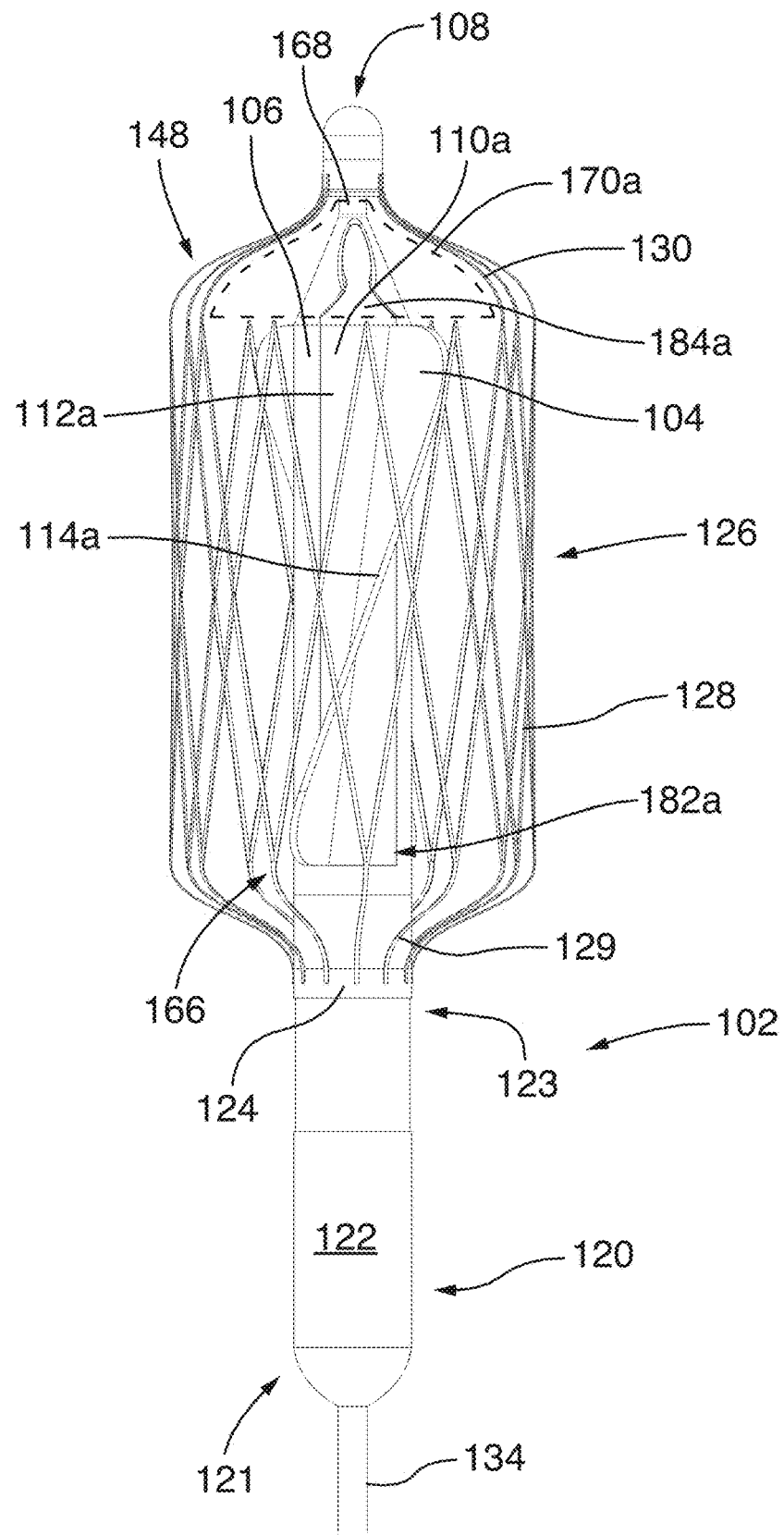
FIG. 21 is a side elevation view of the blood pump of FIG. 4 with the fully assembled impeller shown in FIGS. 18 & 19.
Figure 22:
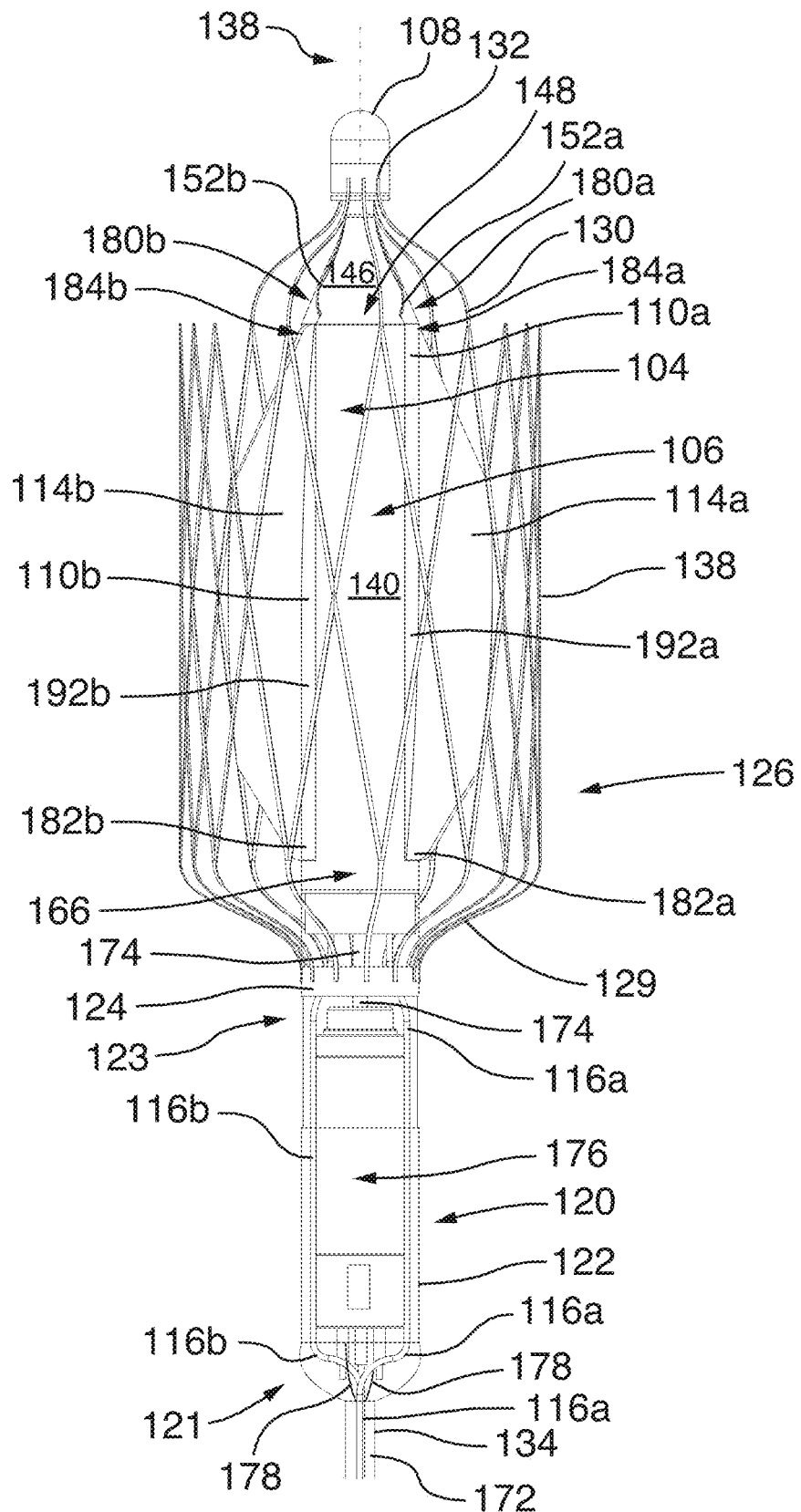
FIG. 22 is a side elevation view of the blood pump of FIG. 4, similar to FIG. 21, but with the housing of the drive unit and the control cable being shown as transparent.

Referring to FIG. 21, attached to the impeller hub module 106 is a drive unit 120. The drive unit 120 has a housing 122 containing an electric motor 176 and a drive shaft 174. The electric motor 176 drives the drive shaft 174, and the drive shaft 174 drives the impeller 104. In this embodiment, the housing 122 an elongate generally right circular cylindrical in shape, having a diameter which is generally the same as the diameter of the impeller hub module 106 (and thus the hub 105 of the impeller 104). In this embodiment the impeller hub module 106 and the drive unit 120 are connected together to form single implantable unit 102 (as they are implanted and explanted as a single unit in this embodiment).

At the proximal end 121 of the drive unit 120, extending proximally, is a control cable 134. The control cable 134 is hollow, having a lumen 172 therein. The lumen 172 communicates with the interior of the housing 122 containing the motor 176. Electrical wiring 178 for providing electricity to power the motor 176 extends from the motor 176 through the cavity of the housing 122 and then through the lumen 172 of the control cable 134 to the proximal end unit 136 of the device 100, where the wiring can be put into electric communication with an appropriate power source. The control cable 134 is of a conventional design.

Anchor

Referring to FIGS. 17, 18, 19, and 20, attached to the housing 122 of the drive unit 120 is a wire network anchor 126. In this embodiment, anchor 126 is a wire network having a compact configuration and an expanded configuration. In the expanded configuration, the anchor 126 exerts a force on the walls of the conduit into which the device 100 has been implanted. That force is sufficient to anchor the device 100 in place within the conduit when the device is being assembled, disassembled, and operating normally. Further, in the expanded configuration the wire network is sized and dimensioned such that the impeller 104 is able to rotate during normal operation of the device 100 without contacting the wire network (or any other part of the anchor 126) nor the conduit itself.

The wire network 126 has three different groups of wires. It is the second group of wires 128 that abut up against the walls of the conduit into which the device has been implanted in order to secure the device 100 in place. As can be seen in the Figs., in this embodiment when the anchor 126 is in the expanded configuration the wires of the second group 128 generally surround the impeller 104.

Proximal to the wires of the second group 128 are wires of the first group 129. At their distal end (unlabeled), wires of the first group 129 connect to and extend proximally from the wires of the second group 128. At their proximal end (unlabeled) wires of the first group 129 are connected to a metal band 124 that is non-moveably affixed to the housing 122 of the drive unit 102. The housing 122 of the drive unit 120 does not rotate when the device 100 is in operation and the impeller 104 is rotating.

Figure 20:
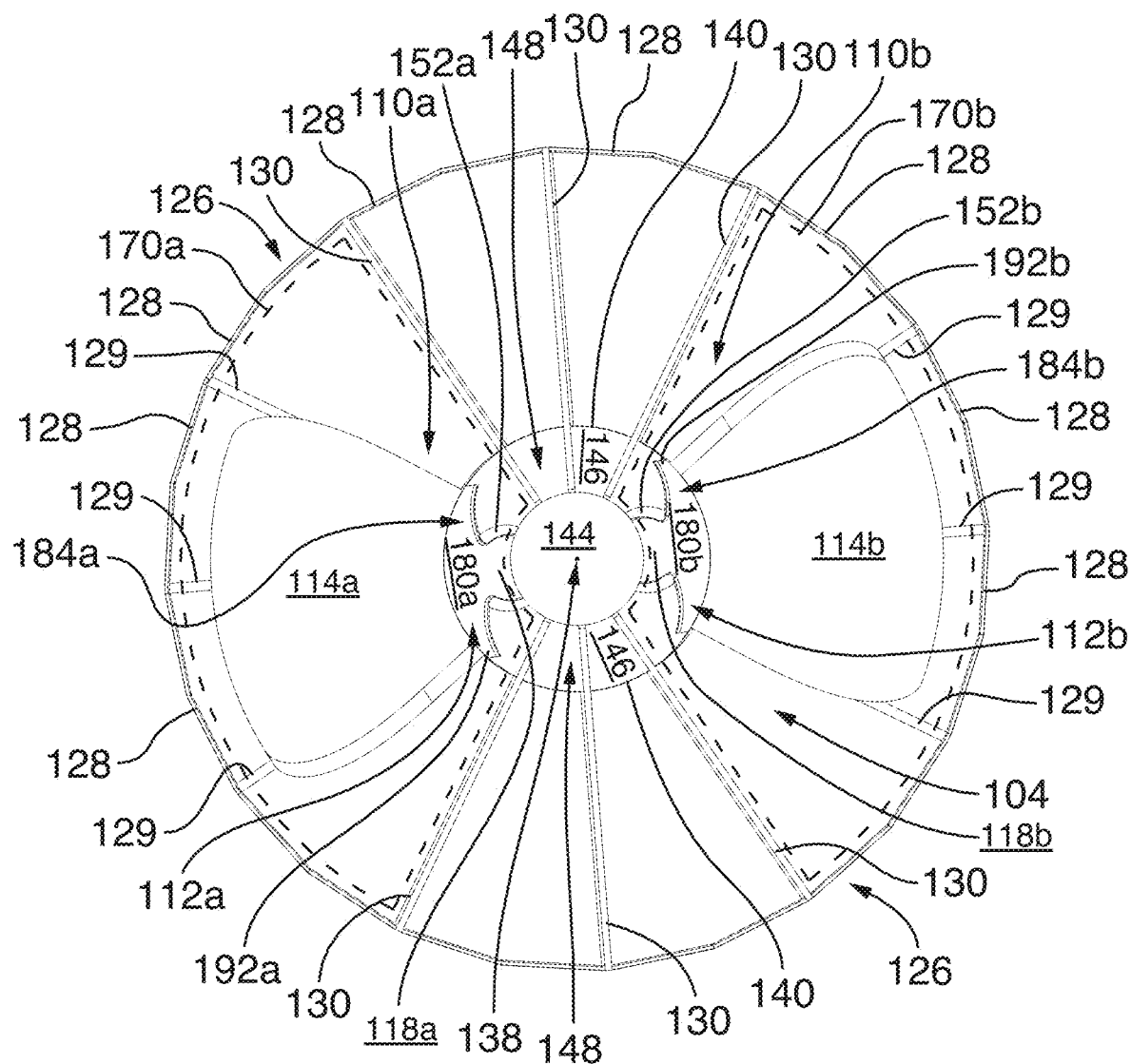
FIG. 20 is a plan view of the distal end of the fully assembled impeller shown in FIGS. 18 & 19.

Distal to the wires of the second group 128 are wires of the third group 130. At their proximal end (unlabeled), wires of the third group 130 connect to and extend distally from the wires of the second group 128. At the distal end (unlabeled) wires of the third group 130 are connected to a metal band 132 that is non-moveably affixed to the distal tip body 108. The distal tip body 108, rotatably holds the distal spindle 168 of the impeller hub module 106, allowing the impeller 104 to rotate without rotating the distal tip body 108. Referring to FIGS. 20 and 21, there are gaps 170a, 170b in the wires of the third group 130 that allow for the passage of the impeller vane modules 110a, 110b (respectively) from outside of the wire network of the anchor 126 to inside of the wire network of the anchor 126 as will be explained in further detail hereinbelow.

In this embodiment, the anchor 126 is made of nitinol, which is a shape memory alloy. It is the "shape memory" of the nitinol which causes the bias of the wire network 126 of the anchor to its expanded configuration.

Control Wires

Referring to FIGS. 8, 9, 10, 13, 15, 16, 21, and 23 a first control wire 116a is attached to the first impeller vane module 110a and a second control wire 116b is attached to the second impeller vane module 110b.

Figure 13:
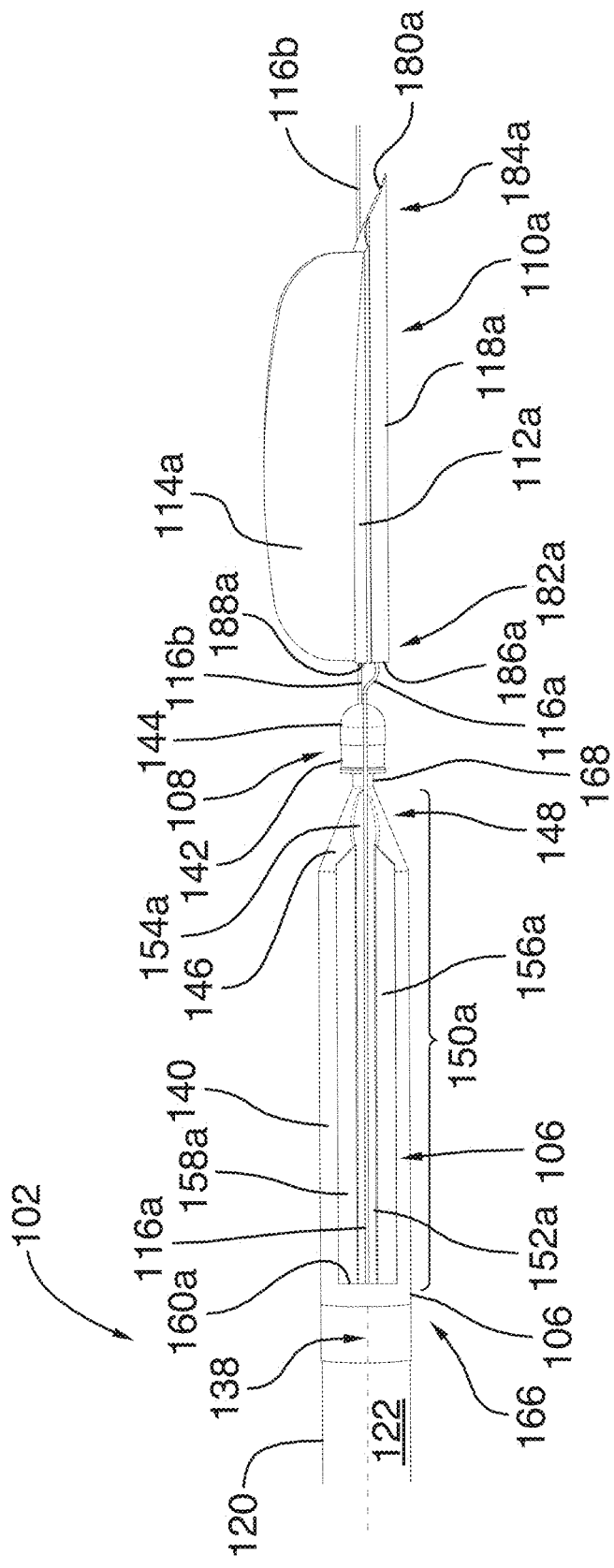
FIG. 13 is a side elevation view of the impeller hub module and a first impeller vane module of the blood pump of FIG. 4, in an unassembled configuration.
Figure 14:
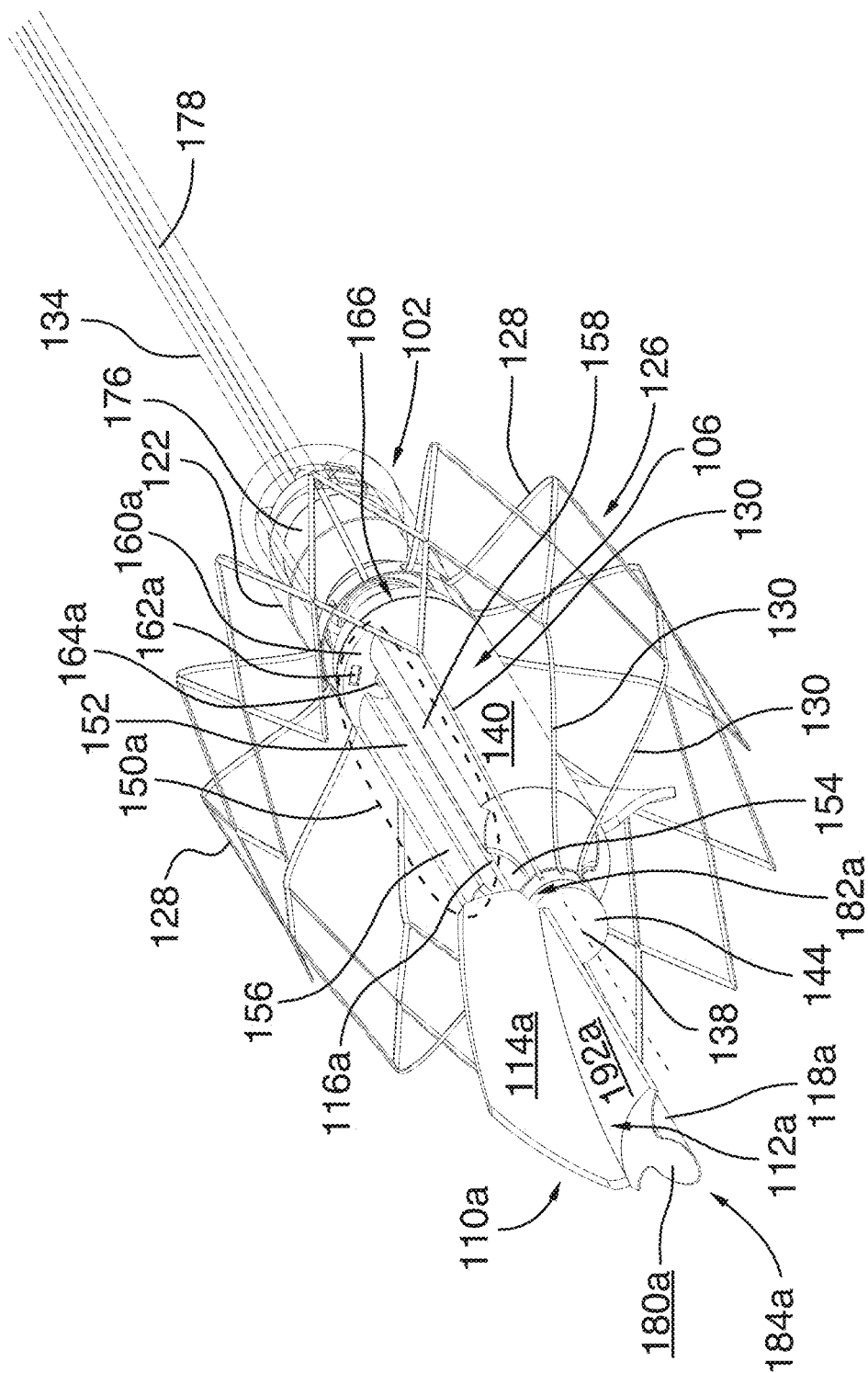
FIG. 14 is an isometric view of blood pump of FIG. 4, with the first impeller vane being pulled towards its assembled configuration.
Figure 23:
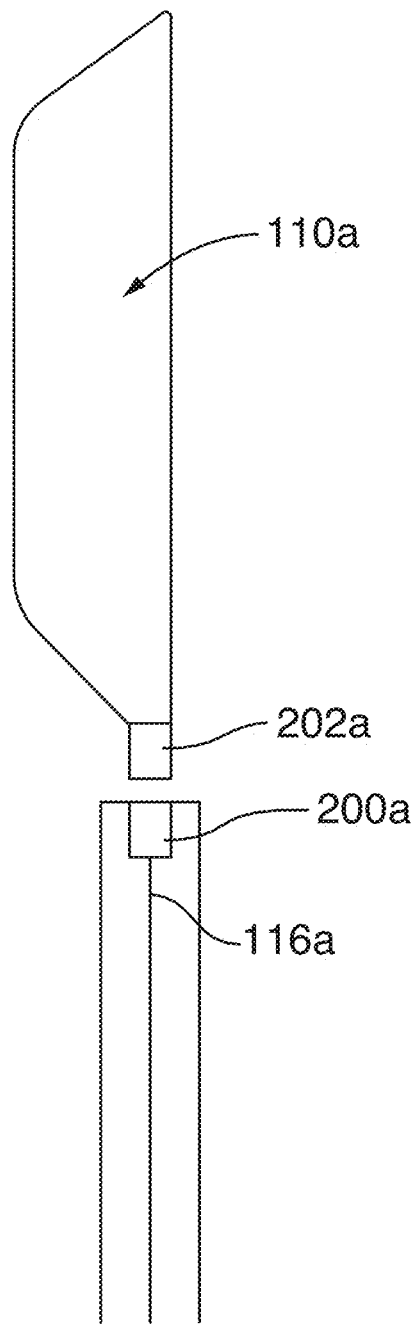
FIG. 23 is a schematic view of the distal end of the first control wire and the interior of the first impeller vane unit.

Referring to FIGS. 8, 13 and 23, the distal end 117a of the first control wire 116a enters the interior of the first impeller vane module 110a through the hole 190a in the proximal end wall 186a of the proximal end 182a of first impeller vane module 110a. At the distal end 117a of the first control wire 116a there is a magnet 200a which is in magnetic connection with magnet 202a within the interior of the first impeller vane module 110a. The magnetic connection between magnet 200a and 202a releasably secures the distal end 117a of the first control wire 116a in place within the interior of the first impeller vane module 110a.

Figure 15:
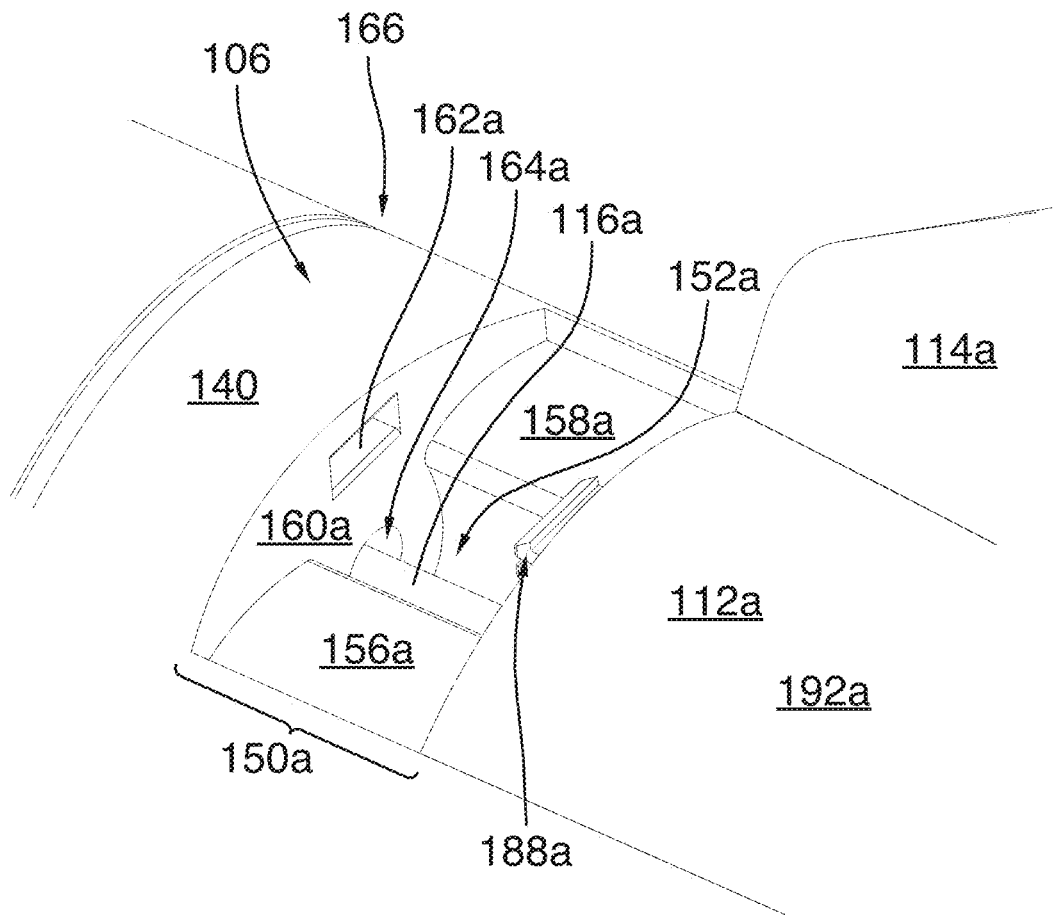
FIG. 15 is an isometric close-up view of the proximal end of the first impeller vane module and the proximal end of the impeller hub module as the first impeller vane module is approaching its assembled configuration.
Figure 16:
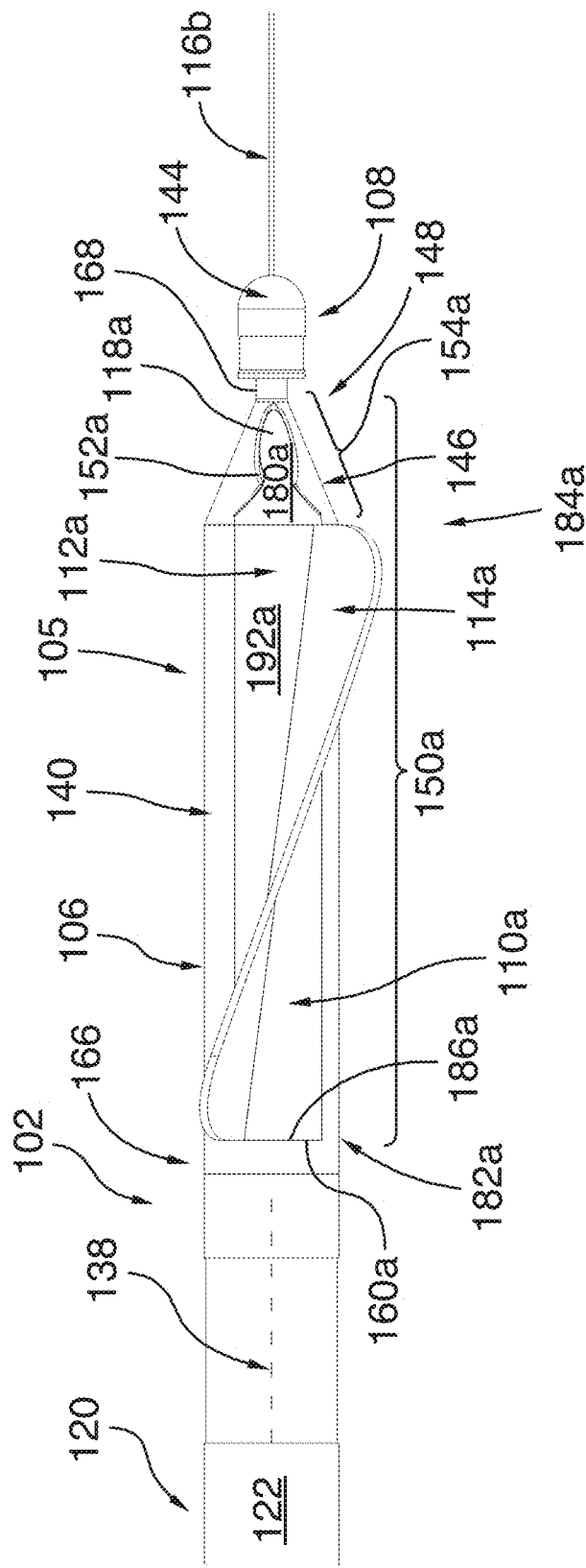
FIG. 16 is a side elevation view of the impeller hub module and the first impeller vane module of the blood pump of FIG. 4, in the assembled configuration, with second impeller vane (not shown) being in an unassembled configuration.

Referring particularly to FIG. 13, the first control wire 116a then extends proximally through the distal opening 154a into the channel 152a of the first impeller hub module connector 150a. Referring particularly to FIG. 15, the first control wire 116a then enters the opening 164a in the wall 160a at the proximal end of the first impeller hub module connector 150a. Finally, referring to FIG. 21, the first control wire 116a passes through a passage (not shown) which starts at the opening 164a in the wall 160a, passes through the body of the impeller hub module 106 and ends up at the very end of the proximal end 166 of the impeller hub module 106. The first control wire 116a then passes through the housing 122 of the drive unit 120 (from its distal end 123 to its proximal end 121) and passes into the lumen 172 of the control cable 134. The first control wire 116a finally passes through the control cable 134 and is accessible by the surgeon at the proximal end unit 136.

Similarly, the distal end 117b of the second control wire 116b enters the interior of the second impeller vane module 110b through the hole 190b in the proximal end wall 186b of the proximal end 182b of second impeller vane module 110b. At the distal end 117b of the second control wire 116b there is a magnet 200b which is in magnetic connection with magnet 202*b* within the interior of the second impeller vane module 110*b*. The magnetic connection between magnet 200*b* and 202*b* releasably secures the distal end 117*b* of the second control wire 116*b* in place within the interior of the second impeller vane module 110*b*.

The second control wire 116*b* then extends proximally through the distal opening 154*b* into the channel 152*b* of the second impeller hub module connector 150*b*. The second control wire 116*b* then enters the opening 164*b* in the wall 160*b* at the proximal end of the second impeller hub module connector 150*b*. Finally, referring to FIG. 21, the second control wire 116*b* passes through a passage (not shown) which starts at the opening 164*b* in the wall 160*b*, passes through the body of the impeller hub module 106 and ends up at the very end of the proximal end 166 of the impeller hub module 106. The first control wire 116*b* then passes through the housing 122 of the drive unit 120 (from its distal end 123 to its proximal end 121) and passes into the lumen 172 of the control cable 134. The second control wire 116*b* finally passes through the control cable 134 and is accessible by the surgeon at the proximal end unit 136.

Implantation, Operation & Explantation of the Device

Device 100 can be transcatheterly implanted and explanted using standard conventional techniques. (The WO '765 Publication provides a very detailed description of such techniques, and they are not repeated herein for the sake of brevity).

Figure 9:
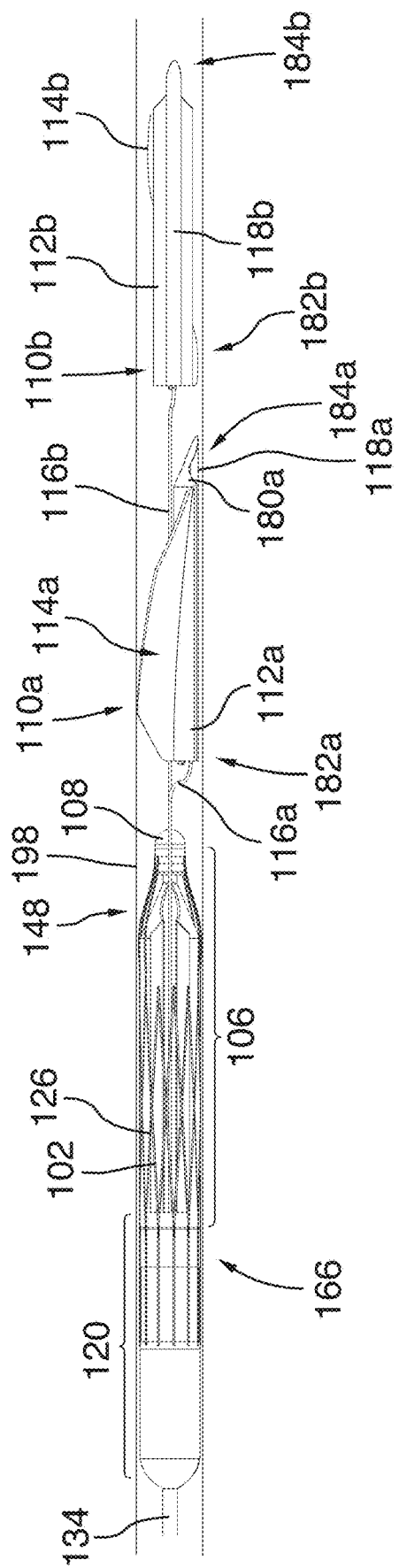
FIG. 9 is view of a single implantable unit (motor housing, impeller hub, anchor) and two impeller vane units in an unassembled configuration of the blood pump of FIG. 4, within a delivery sheath (with the anchor being in the compact configuration), with part of the delivery sheath having been cut away to show the components inside.

As the skilled addressee would be aware, the implantation of device 100 typically starts with device 100 being inside a loader. Although FIG. 9 shows device 100 inside a delivery sheath 198 (being particular type of catheter), the device 100 when inside a loader would look essentially the same. In FIG. 9, the distal end of the loader (198) is on the right of the figure and the proximal end of the loader (198) is on the left of the figure. Closest to the distal end of the loader (198) is the second impeller vane module 110*b*. The second impeller vane module 110*b* has the same orientation in the loader (198) as the device 100 itself. Thus, the distal end 184*b* of the second impeller vane module 110*b* is closest to the distal end of the loader (198). When in the loader, the second impeller vane module 110*b* is in an unassembled configuration with respect to the impeller hub module 106.

Immediately proximal to the second impeller vane module 110*b* in the loader (198) is the first impeller vane module 110*a*. The first impeller vane module 110*a* has the same orientation in the loader (198) as the device 100 itself. Thus, the distal end 184*a* of the first impeller vane module 110*a* is adjacent the proximal end 182*b* of the second impeller vane module 110*b*. When in the loader (198), the second impeller vane module 110*a* is in an unassembled configuration with respect to the impeller hub module 106.

Immediately proximal to the first impeller vane module 110*b* is the single implantable unit 102, which combines the impeller hub module 106 and the drive unit 120. The single implantable unit 102 has the same orientation in the loader (198) as the device 100 itself. Thus, the distal end 148 of the impeller hub module 106 is adjacent the proximal end 182*a* of the first impeller vane module 110*a*. The proximal end 121 of the drive unit 120 is closest to the proximal end of the loader (198). The control cable 134 extends proximally from the proximal end 121 of the drive unit 120 to the proximal end unit 136. The wire network anchor 126 is in its collapsed configuration within the loader (198).

The second control wire 116*b* extends from the proximal end 182*b* of the second impeller vane module 110*b*, passes by the first impeller vane module 110*a*, passes into the channel 152*b* of the second impeller hub connector 150*b* of the impeller hub module 106, extends through the housing 122 of the drive unit 120, enters the lumen 172 of the control cable 134 and extends to the proximal end unit 136 of the device 100. Similarly, the first control wire 116*a* extends from the proximal end 182*a* of the first impeller vane module 110*a*, passes into the channel 152*a* of the first impeller hub connector 150*a* of the impeller hub module 106, extends through the housing 122 of the drive unit 120, enters the lumen 172 of the control cable 134 and extends to the proximal end unit 136 of the device 100.

As a non-limiting example, in a device 100 to be implanted in a patient to provide left heart support, the delivery site of the device 100 may be within thoracic descending aorta. Thus, at a high level and broadly speaking, the device 100 can be implanted by the surgeon in the following manner by: (1) Obtaining access to the femoral artery of the patient (e.g., via the well-known Seldinger technique). (2) Guiding a delivery sheath 198 to the delivery site (e.g., using a conventional guidewire and railing the delivery sheath 198 along the guidewire). (3) Inserting the impeller vane modules 110*b*, 110*a* in their unassembled configuration distal end 184*b*, 184*a* first into the delivery sheath 198 in series one after another (e.g., from a loader in which they are in the configuration described above). (4) Inserting the single implantable unit 102 (which includes impeller hub module 106) into the delivery sheath 198 (e.g., again from a loader in which the single implantable unit 102 is in the configuration described above). (5) Guiding the impeller vane modules 110*b*, 110*a* and the single implantable unit 102 within the delivery sheath 198 to the delivery site. (6) Promoting exit of the impeller vane modules 110*b*, 110*a* from the delivery sheath 198 at the delivery site (e.g., by partially withdrawing the delivery sheath 198 while keeping the impeller vane modules 110*b*, 110*a* in place (e.g., via their control wires 116*b*, 116*a*). (7) Promoting exit of the single implantable unit 102 from the delivery sheath 198 at the delivery site. In the embodiment of the device 100 described above, this causes the wire network anchor 126 to adopt its expanded configuration, anchoring the single implantable unit 102 (of which the impeller hub module 106 is a part) in place. (8) Withdrawing the delivery sheath 198 from the body.

Figure 10:
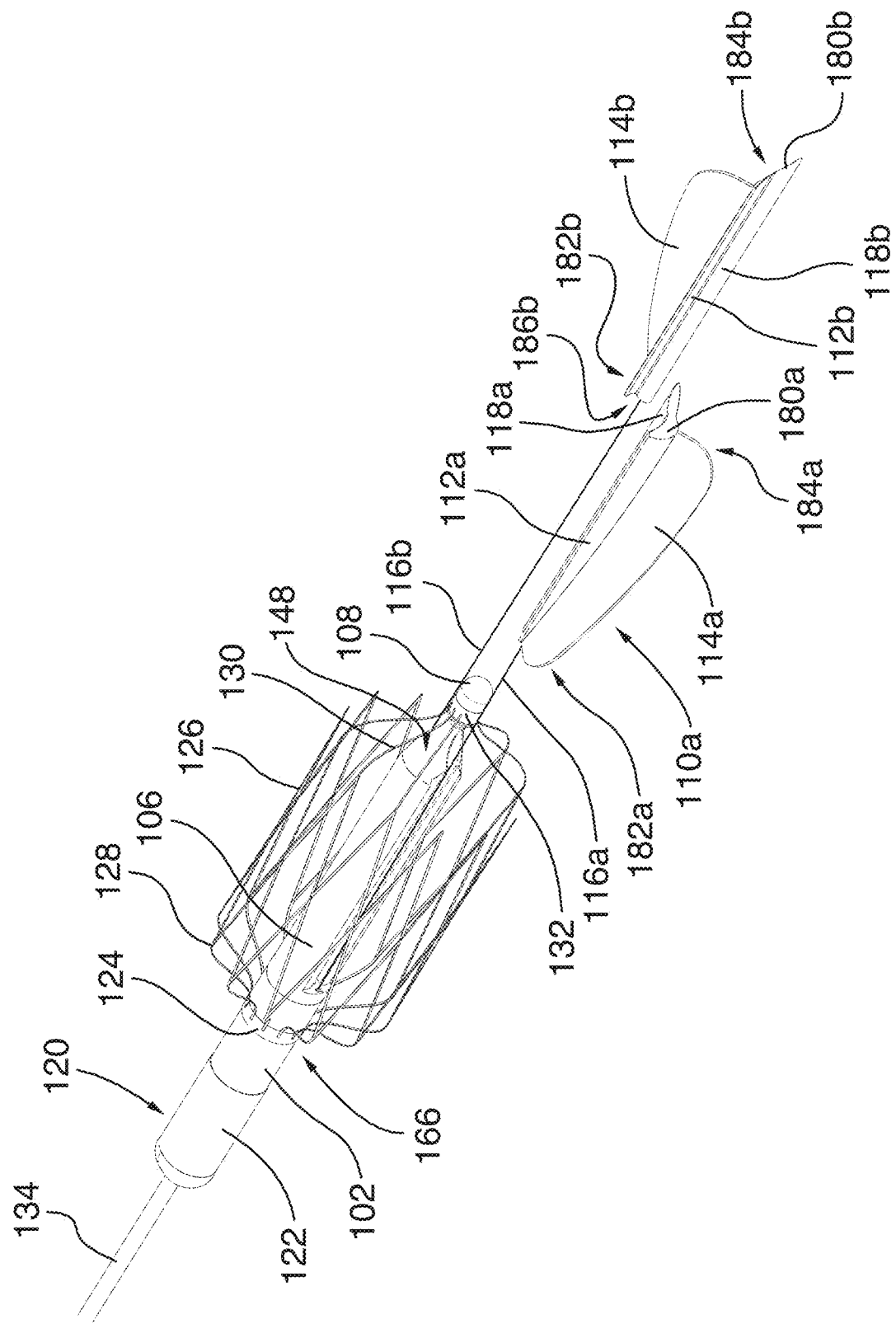
FIG. 10 is an isometric view of the blood pump of FIG. 4, taken from the distal end thereof, with both of the impeller pump modules in an unassembled configuration.
Figure 11:
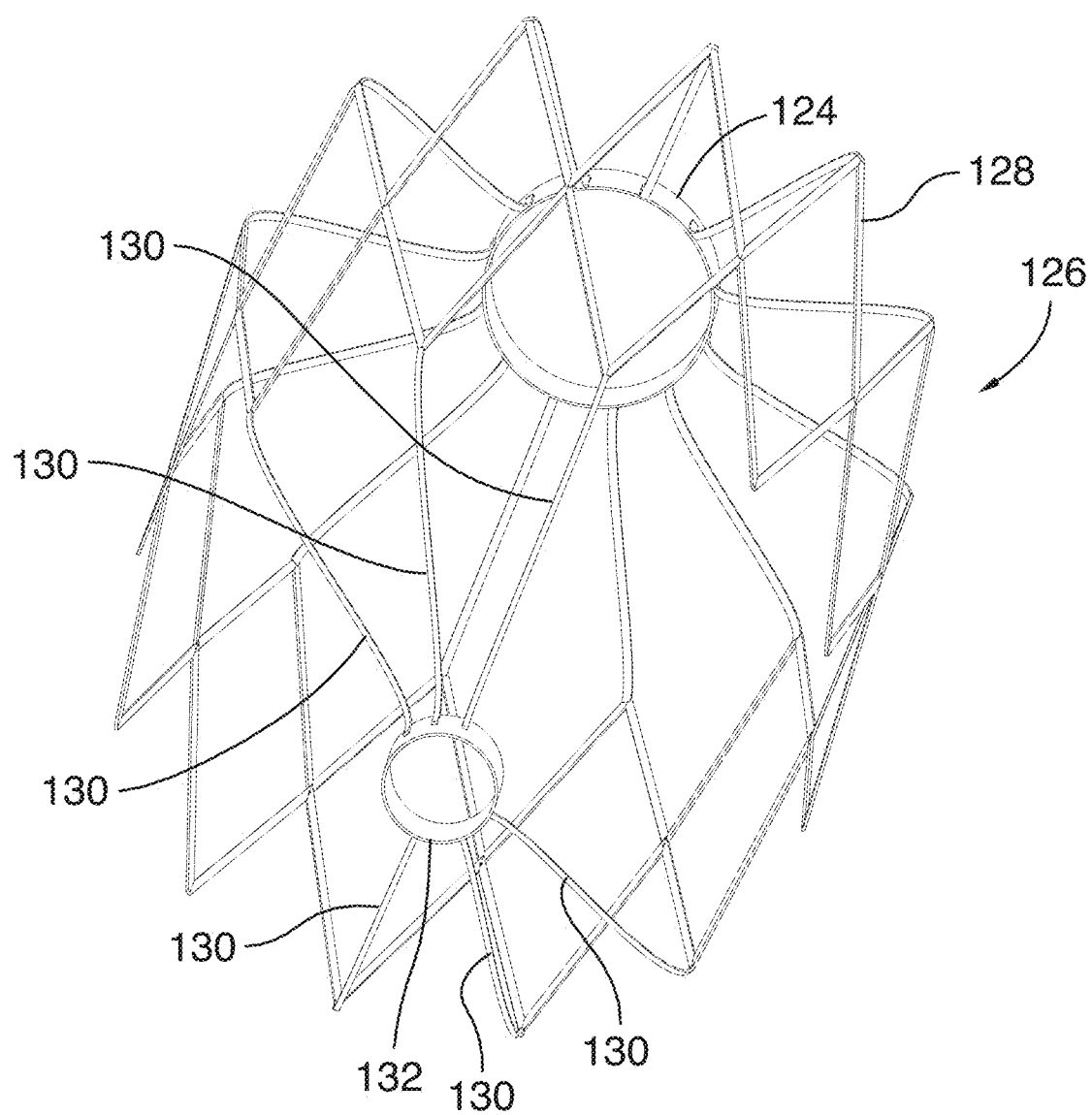
FIG. 11 is an isometric view of the anchor of the blood pump of FIG. 4, in its expanded configuration, taken from the distal end thereof.
Figure 12:
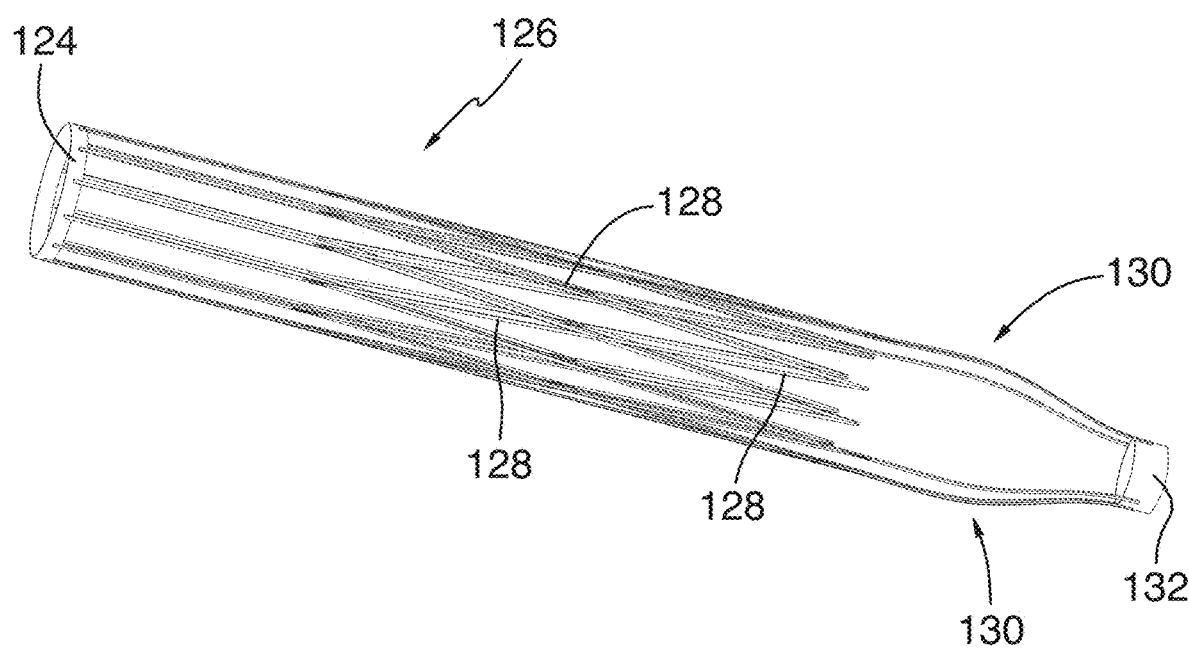
FIG. 12 is an isometric view of the anchor of the blood pump of FIG. 4, in its compact configuration, taken from towards the proximal end thereof.

In the next part of the implantation process, the impeller 104 of the device 100 is assembled in vivo at the delivery site. FIG. 10 illustrates the configuration of the device 100 just after delivery as described hereinabove. The surgeon then manipulates the first control wire 116*a* of the first impeller vane module 110*a* to bring the first impeller vane module 110*a* into its assembled configuration with respect to the impeller hub module 106. As can be well seen in FIGS. 20 & 21, when the wire network of the anchor 126 is in its expanded configuration gaps 170*a*, 170*b* are formed in the wires of the third group 130 that allow for the passage of the impeller vane modules 110*a*, 110*b* (respectively) from outside of the wire network of the anchor 126 to inside of the wire network of the anchor 126. Thus, the surgeon pulls the first control wire 116*a* of the first impeller vane module 110*a* to move the first impeller vane module 110*a* from a position outside of and distal to the wire network of the anchor 126 to a position where the first impeller vane module 110*a* starts to move through the gap 170*a* and starts to slide into its assembled configuration. Specifically, the right circular cylinder portion 193*a* of the first impeller vane module connector 118*a* enters the opening 154*a* of the channel 152*a* of the first impeller hub module connector 150*a*. As the surgeon continues to pull the first control wire 116*a*, the first impeller vane module 110*a* continues to slide closer to the proximal end wall of 160a of the first impeller hub module connector 150a. Thus, the right circular cylinder portion 193a of the first impeller vane module connector 118a continues to travel within the channel 152a of the first impeller hub module connector 150a. Referring now to FIG. 15, eventually the detent 188a of the secondary connector 189a projecting from the proximal end wall 186a enters the cavity 162a of the secondary connector 189a and is releasably retained therein. At this point, the proximal end wall 186a of the proximal end 182a of the first impeller vane module 110a completely abuts the proximal end wall 160a of the first impeller hub connector 150a. At this point, first impeller vane module 110a is in its assembled configuration with respect to the impeller hub module 106. The first impeller vane module 110a is retained in its assembled configuration as a result of the dovetail joint formed by the right circular cylinder portion 193a of the first impeller vane module connector 118a and the channel 152a of the first impeller hub module connector 150a, and as a result of the detent 188a of the secondary connector 189a being retained in the cavity 162a.

Next, the surgeon manipulates the second control wire 116b of the second impeller vane module 110b to bring the second impeller vane module 110b into its assembled configuration with respect to the impeller hub module 106. Referring again to FIGS. 20 & 21, when the wire network of the anchor 126 is in its expanded configuration gaps 170a, 170b are formed in the wires of the third group 130 that allow for the passage of the impeller vane modules 110a, 110b (respectively) from outside of the wire network of the anchor 126 to inside of the wire network of the anchor 126. Thus, the surgeon pulls the second control wire 116b of the second impeller vane module 110b to move the second impeller vane module 110b from a position outside of and distal to the wire network of the anchor 126 to a position where the second impeller vane module 110b starts to move through the gap 170b and starts to slide into its assembled configuration. Specifically, the right circular cylinder portion 193b of the second impeller vane module connector 118b enters the opening 154b of the channel 152b of the second impeller hub module connector 150b. As the surgeon continues to pull the second control wire 116b, the second impeller vane module 110b continues to slide closer to the proximal end wall of 160b of the second impeller hub module connector 150b. Thus, the right circular cylinder portion 193b of the second impeller vane module connector 118b continues to travel within the channel 152b of the second impeller hub module connector 150b. Referring now to FIG. 15, eventually the detent 188b of the secondary connector 189b projecting from the proximal end wall 186b enters the cavity 162b of the secondary connector 189b and is releasably retained therein. At this point, the proximal end wall 186b of the proximal end 182b of the second impeller vane module 110b completely abuts the proximal end wall 160b of the second impeller hub connector 150b. At this point, second impeller vane module 110b is in its assembled configuration with respect to the impeller hub module 106. The second impeller vane module 110b is retained in its assembled configuration as a result of the dovetail joint formed by the right circular cylinder portion 193b of the second impeller vane module connector 118b and the channel 152b of the second impeller hub module connector 150b, and as a result of the detent 188b of the secondary connector 189b being retained in the cavity 162b.

Figure 17:
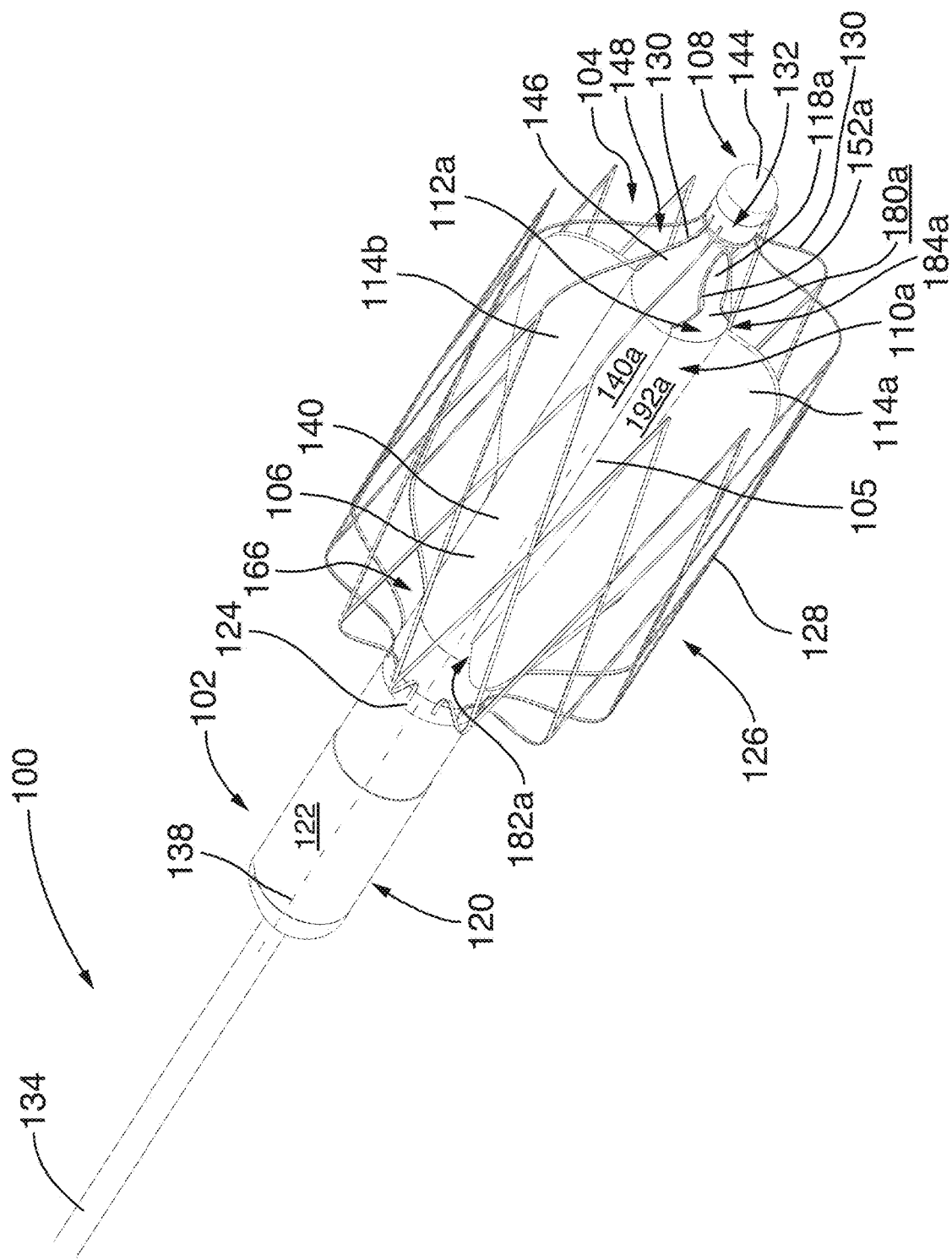
FIG. 17 is an isometric view of the blood pump of FIG. 4, taken from the distal end thereof, with both the first impeller vane module and the second impeller vane module being their assembled configurations such that the impeller is fully assembled.

As can be well seen in FIGS. 17 to 19, when each of the first impeller vane module 110a and the second impeller vane module 110b is retained in its assembled configuration, the impeller 104 is fully assembled. Further, the outer surface 140 of the impeller hub module 106 is complete such that the impeller hub 105 (but for the vanes 114a, 114b) has the shape of a right circular cylinder. The tapered portion 146 of the distal end 148 of the impeller hub module 106 is now complete as well.

The surgeon then pulls on the first control wire 116a with sufficient force to overcome the magnetic connection holding the first control wire 116a in place within the interior of the first impeller vane module 110a. Thus, magnet 200a becomes disconnected from magnet 202a. The surgeon continues to pull the first control wire 116a until the distal end 117a of the first control wire 116a including magnet 200a have exited the passage at the proximal end 166 of the impeller hub module 106. The distal end 117a of the first control wire 116a including magnet 200a are now within the housing 122 of the drive unit 120 at the distal end 123 of the drive unit 120. The distal end 117a of the first control wire 116a including magnet 200a remain in that position, completely clear of the impeller 104, during operation of the impeller 104. The impeller 104 is thus free to rotate without interference from the first control wire 116a and magnet 200a.

Finally, the surgeon pulls on the second control wire 116b with sufficient force to overcome the magnetic connection holding the second control wire 116a in place within the interior of the second impeller vane module 110b. Thus, magnet 200b becomes disconnected from magnet 202b. The surgeon continues to pull the second control wire 116b until the distal end 117b of the second control wire 116b including magnet 200b have exited the passage at the proximal end 166 of the impeller hub module 106. The distal end 117b of the second control wire 116b including magnet 200b are now within the housing 122 of the drive unit 120 at the distal end 123 of the drive unit 120. The distal end 117b of second the control wire 116b including magnet 200b remain in that position, completely clear of the impeller 104, during operation of the impeller 104. The impeller 104 is thus free to rotate without interference from the second control wire 116b and magnet 200b.

The impeller 104 and thus the device 100 are now operable. The operative of the device 100 is conventional.

In explanation of the device 100, the device 100 is first disassembled, by reversing the assembly process described above. Once the device has been disassembled it is conventionally retrieved using snare and a retrieval sheath as described in the WO '765 Publication.

MISCELLANEOUS

The present technology is not limited in its application to the details of construction and the arrangement of components set forth in the preceding description or illustrated in the drawings. The present technology is capable of other embodiments and of being practiced or of being carried out in various ways. Also, the phraseology and terminology used herein is for the purpose of description and should not be regarded as limiting. The use of "including", "comprising", or "having", "containing", "involving" and variations thereof herein, is meant to encompass the items listed thereafter as well as, optionally, additional items. In the description the same numerical references refer to similar elements.

It must be noted that, as used in this specification and the appended claims, the singular form "a", "an" and "the" include plural referents unless the context clearly dictates otherwise.

As used herein, the term "about" or "generally" or the like in the context of a given value or range (whether direct or indirect, e.g., "generally in line", "generally aligned", "generally parallel", etc.) refers to a value or range that is within 20%, preferably within 10%, and more preferably within 5% of the given value or range.

As used herein, the term "and/or" is to be taken as specific disclosure of each of the two specified features or components with or without the other. For example, "A and/or B" is to be taken as specific disclosure of each of (i) A, (ii) B and (iii) A and B, just as if each is set out individually herein.

Modifications and improvements to the above-described implementations of the present technology may become apparent to those skilled in the art. The foregoing description is intended to be exemplary rather than limiting. The scope of the present technology is therefore intended to be limited solely by the scope of the appended claims.

The invention claimed is:

1. A modular impeller device configured to be implanted within a body of a patient, the modular impeller device comprising:
    an impeller hub;
    an impeller vane; and
    a control wire configured to be attached to the impeller vane,
wherein the modular impeller device has an assembled configuration in which the impeller vane is mated with the impeller hub, and an unassembled configuration in which the impeller vane is unmated with the impeller hub, the control wire being movable relative to the impeller hub to transition the modular impeller device within the body from the unassembled configuration to the assembled configuration, when the control wire is attached to the impeller vane.

2. The modular impeller device according to claim 1, wherein the control wire is slidably movable relative to the impeller hub.

3. The modular impeller device according to claim 1, wherein the impeller hub comprises a passage configured for slidably receiving the control wire therealong.

4. The modular impeller device according to claim 1, wherein the control wire is configured for being pulled to move the control wire relative to the impeller hub for transitioning the modular impeller device within the body from the unassembled configuration to the assembled configuration.

5. The modular impeller device according to claim 1, wherein the control wire is further movable relative to the impeller hub to transition the modular impeller device within the body from the assembled configuration to the unassembled configuration, when the control wire is attached to the impeller vane.

6. The modular impeller device according to claim 5, wherein the control wire is configured for being pushed to move the control wire relative to the impeller hub for transitioning the modular impeller device within the body from the assembled configuration to the unassembled configuration.

7. The modular impeller device according to claim 1, wherein the control wire is configured for releasably attaching the impeller vane.

8. The modular impeller device according to claim 7, wherein the modular impeller device, when in the assembled configuration, is configured for being operated when the control wire is released from the impeller hub.

9. The modular impeller device according to claim 1, wherein the control wire comprises a first magnet, and the impeller vane comprises a second magnet magnetically releasably attachable to the first magnet.

10. The modular impeller device according to claim 1, wherein the impeller hub comprises an impeller hub connector, and the impeller vane comprises an impeller vane connector configured for releasably connecting to the impeller vane connector.

11. The modular impeller device according to claim 10, wherein the impeller hub connector comprises a channel, and the impeller vane connector comprises a cylinder portion configured for being slidably received in the channel.

12. The modular impeller device according to claim 11, wherein the control wire is disposed at least partially along the channel.

13. The modular impeller device according to claim 1, further comprising a secondary connector configured for releasably retaining the impeller hub and the impeller vane together.

14. The modular impeller device according to claim 1, further comprising an anchor sized and shaped for surrounding at least partially the impeller hub, the anchor having a collapsed configuration for transcatheter delivery of the modular impeller device within the body, and an expanded configuration configured for anchoring the modular impeller device intravascularly within the body.

15. The modular impeller device according to claim 14, wherein the control wire passes through an opening of the anchor.

16. The modular impeller device according to claim 15, wherein the opening of the anchor is sized and shaped for passing the impeller vane therethrough.

17. The modular impeller device according to claim 1, further comprising a motor unit and a drive shaft operatively connected between the motor unit and the impeller hub for driving the impeller hub.

18. The modular impeller device according to claim 17, further comprising a control cable extending distally from the motor unit, the control cable having a lumen configured for receiving the drive shaft and the control wire therein.

19. The modular impeller device according to claim 17, further comprising a control cable extending proximally from the motor, the control cable having a lumen configured for receiving the control wire therein.

20. The modular impeller device according to claim 1, wherein the control wire is manipulable at a distal end portion thereof by an operator for moving the control wire relative to the impeller hub within the body.

21. The modular impeller device according to claim 20, wherein the distal end portion is configured to be disposed extracorporeally when the modular impeller device is implanted within the body.

22. The modular impeller device according to claim 1, wherein the modular impeller device is transcatheterly implantable.

23. The modular impeller device according to claim 1, wherein the impeller hub and the impeller vane are assemblable together within a cardiovascular system of the patient.

24. The modular impeller device according to claim 1, wherein the control wire is further configured to be removably attached to the impeller vane, impeller is rotatable only when the control wire is removed from the impeller vane.

25. A modular impeller device configured to be implanted within a cardiovascular system of a patient, the modular impeller device comprising:
    an impeller including an impeller hub and an impeller vane;

an anchor configured to at least partially surround the impeller and to anchor the modular impeller device within the cardiovascular system; and a control wire configured to be removably attached to the impeller vane, and further configured to be manipulated from outside the cardiovascular system by an operator for the impeller vane to mate with the impeller hub within the cardiovascular system, and for the impeller vane to unmate from the impeller hub within the cardiovascular system when the control wire is attached to the impeller vane.

26. The modular impeller device according to claim 25, wherein the control wire is further configured for the impeller vane to slidably mate with the impeller hub, and for the impeller vane to slidably unmate from the impeller hub.

27. The modular impeller device according to claim 26, wherein the impeller is rotatable only when the control wire is removed from the impeller vane.

28. A modular impeller device configured to be implanted within a cardiovascular system of a patient, the modular impeller device comprising:

an impeller hub;

an impeller vane; and a control wire releasably attachable to the impeller vane, wherein the modular impeller device has an assembled configuration in which the impeller vane is mated with the impeller hub, and an unassembled configuration in which the impeller vane is unmated with the impeller hub, the control wire being actuatable to transition the modular impeller device within the cardiovascular system from the unassembled configuration to the assembled configuration, when the control wire is attached to the impeller vane.

29. The modular impeller device according to claim 28, wherein the control wire is slidably actuatable for transitioning the modular impeller device within the cardiovascular system from the unassembled configuration to the assembled configuration.

30. The modular impeller device according to claim 29, wherein the impeller hub is rotatable only when the control wire is removed from the impeller vane.

* * * * *